(12) United States Patent
Maharbiz et al.

(10) Patent No.: US 10,463,293 B2
(45) Date of Patent: Nov. 5, 2019

(54) METHODS AND APPARATUS FOR MONITORING WOUND HEALING USING IMPEDANCE SPECTROSCOPY

(71) Applicant: THE REGENTS OF THE UNIVERSITY OF CALIFORNIA, Oakland, CA (US)

(72) Inventors: Michel Maharbiz, El Cerrito, CA (US); Vivek Subramanian, Orinda, CA (US); Ana Claudia Arias, Lafayette, CA (US); Sarah Swisher, El Cerrito, CA (US); Amy Liao, Berkeley, CA (US); Monica Lin, Berkeley, CA (US); Felippe Pavinatto, Albany, CA (US); Yasser Khan, Berkeley, CA (US); Daniel Cohen, Berkeley, CA (US); Elisabeth Leeflang, San Francisco, CA (US); Shuvo Roy, San Francisco, CA (US); Michael Harrison, San Francisco, CA (US); David Young, Mill Valley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 212 days.

(21) Appl. No.: 15/379,220

(22) Filed: Dec. 14, 2016

(65) Prior Publication Data

US 2017/0156658 A1    Jun. 8, 2017

Related U.S. Application Data

(63) Continuation of application No. PCT/US2015/036106, filed on Jun. 16, 2015.
(Continued)

(51) Int. Cl.
*A61B 5/00* (2006.01)
*A61B 5/053* (2006.01)

(52) U.S. Cl.
CPC .............. *A61B 5/445* (2013.01); *A61B 5/053* (2013.01); *A61B 5/7278* (2013.01);
(Continued)

(58) Field of Classification Search
CPC ....... A61B 5/445; A61B 5/0531; A61B 5/053; A61B 5/7278; A61B 2526/046; A61B 2562/164
See application file for complete search history.

(56) References Cited

U.S. PATENT DOCUMENTS 9,220,455 B2    12/2015    Sarrafzadeh et al.
9,398,879 B2    7/2016    Sarrafzadeh et al.
(Continued)

FOREIGN PATENT DOCUMENTS

KR    10-0462498 B1    3/2006

OTHER PUBLICATIONS

Korean Intellectual Property Office (KIPO), International Search Report and Written Opinion dated Sep. 18, 2015, related PCT International Application No. PCT/US2015/036106, pp. 1-16, with claims searched, pp. 17-23. The relevance of non-English language reference KR 10-0462498 is indicated therein.

*Primary Examiner* — Patrick Fernandes
(74) *Attorney, Agent, or Firm* — O'Banion & Ritchey LLP; John P. O'Banion

(57) ABSTRACT

Methods and apparatus for real-time, quantifiable monitoring of high-risk areas of biological tissue are described. The methods and apparatus use impedance spectroscopy to detect subtle changes in tissue health.

13 Claims, 31 Drawing Sheets

Related U.S. Application Data

(60) Provisional application No. 62/013,420, filed on Jun. 17, 2014, provisional application No. 62/012,975, filed on Jun. 16, 2014.

(52) U.S. Cl.
CPC ..... *A61B 2562/04* (2013.01); *A61B 2562/046* (2013.01); *A61B 2562/125* (2013.01); *A61B 2562/164* (2013.01)

(56) References Cited

U.S. PATENT DOCUMENTS

| | | |
|---|---|---|
| 2006/0047218 A1 | 3/2006 | Bloom et al. |
| 2006/0270942 A1* | 11/2006 | McAdams ........... A61B 5/0531 600/547 |
| 2010/0268111 A1 | 10/2010 | Drinan et al. |
| 2013/0123587 A1* | 5/2013 | Sarrafzadeh ........... A61B 5/445 600/306 |
| 2014/0058344 A1 | 2/2014 | Toth |

* cited by examiner

METHODS AND APPARATUS FOR MONITORING WOUND HEALING USING IMPEDANCE SPECTROSCOPY

CROSS-REFERENCE TO RELATED APPLICATIONS

This application is a 35 U.S.C. § 111(a) continuation of PCT international application number PCT/US2015/036106 filed on Jun. 16, 2015, incorporated herein by reference in its entirety, which claims priority to, and the benefit of, U.S. provisional patent application Ser. No. 62/012,975 filed on Jun. 16, 2014, incorporated herein by reference in its entirety, and which also claims priority to, and the benefit of, U.S. provisional patent application Ser. No. 62/013,420 filed on Jun. 17, 2014, incorporated herein by reference in its entirety. Priority is claimed to each of the foregoing applications.

The above-referenced PCT international application was published as PCT International Publication No. WO 2015/195720 on Dec. 23, 2015, which publication is incorporated herein by reference in its entirety.

STATEMENT REGARDING FEDERALLY SPONSORED RESEARCH OR DEVELOPMENT

This invention was made with Government support under 1240380, awarded by the National Science Foundation. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to wound monitoring, and more particularly to monitoring pressure ulcers and wound healing via impedance spectroscopy.

2. Background Discussion

Pressure ulcers are formed by constant pressure or rubbing applied to an area of skin that results in breakdown of the skin and formation of an ulcer. Formation of pressure ulcers is considered a "never event"—an inexcusable, adverse event that occurs in a healthcare setting. Hospitalized patients are prone to developing these ulcers because of the large amounts of time they spend in a bed, where pressure is often localized to certain areas of the body (commonly the sacrum, coccyx, heel, or hips). Patients with diabetes or who are obese are particularly at risk. Hospitals spend billions of dollars each year to prevent formation of pressure ulcers in their patients, as many current solutions (pressure-distributing beds, repositioning patients every few hours, etc.) are incredibly expensive and/or labor-intensive. A device that could sense when a pressure ulcer may form before it forms would provide great cost-savings to hospitals.

Chronic cutaneous wounds affect millions of people each year and take billions of dollars to treat. These patients have wounds that do not follow the natural progression of healing or take greater than 2 months to heal. In these situations, patients often have frequent doctor's visits (on a weekly or more often basis) to monitor the wound healing process and direct treatment. Monitoring of a wound can be very subjective—different doctors have different ways of measuring wound size (ruler, tracing on a sheet of clear plastic), and length of clinical experience can play a significant role in ability to identify relevant wound characteristics. Using a device to take objective measurements of a wound can help direct and standardize patient care. By adding wireless functionality, the monitoring process could also be done remotely, saving patients time and money.

BRIEF SUMMARY

The present description includes an electronic sensing device that utilizes impedance spectroscopy to measure and characterize tissue health, allowing physicians to identify high-risk areas of skin to prevent formation of pressure ulcers, and/or objectively monitor progression of wound healing.

According to one aspect of the present technology, an electronic bandage is described that is capable of mapping the complex impedance across a wound surface using an electrode array. In one embodiment, the electronic bandage may be fabricated using inkjet printing of gold nanoparticle ink onto a flexible PEN substrate. In another embodiment, impedance spectroscopy may be used to measure and characterize tissue health, thus allowing physicians to objectively detect tissue deterioration and intervene before tissue necrosis.

Preliminary data demonstrates that the system and methods of the present description can detect mild pressure-induced damage, even when the damage is not visually apparent. These results show potential for significant improvement in patient outcomes by enabling earlier intervention for pressure ulcers and other chronic skin wounds.

Another aspect is a SMART (Sensing, Monitoring, And Real-Time Analysis of Skin Wounds Using Impedance Spectroscopy) Bandage capable of real-time, quantifiable monitoring of high-risk areas. By using impedance spectroscopy, SMART bandage can detect subtle changes in tissue health, and is configured to sound an alarm when tissue health reaches a threshold level beyond which a pressure ulcer is likely to form. The SMART bandage is capable of significantly improving patient outcomes by enabling earlier intervention prevent pressure ulcer formation.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 9A:
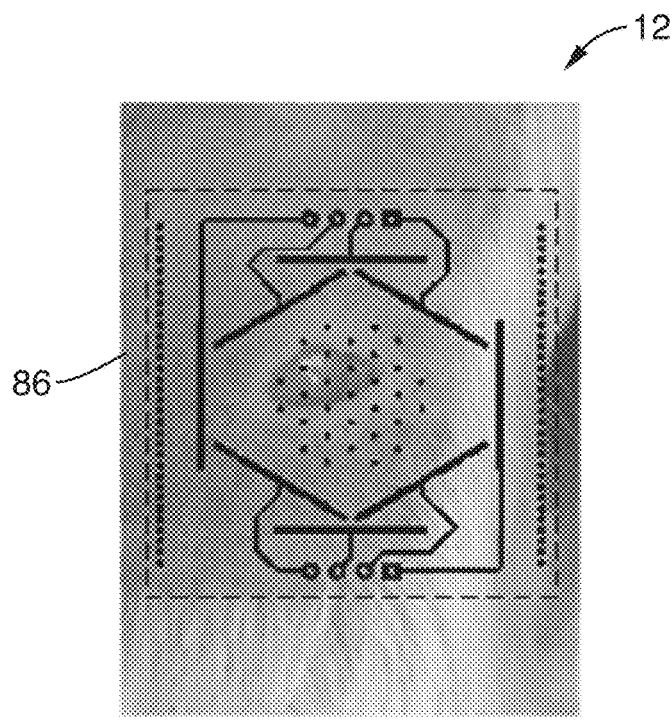
FIG. 9A illustrates an electrode array overlaid on a photo of a wound area.

FIB. 9B shows an exemplary impedance map for the wound of FIG. 9A.

Figure 10A:
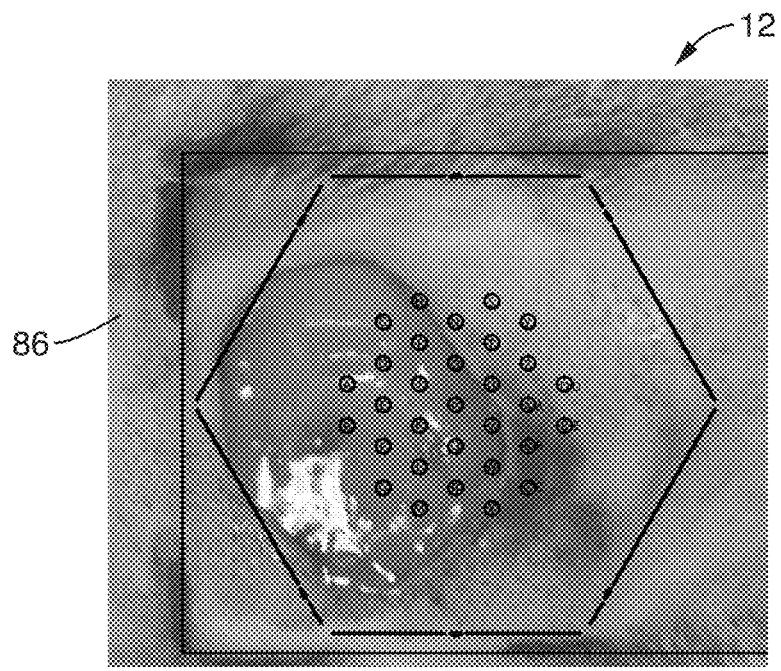

FIG. 10A illustrates an electrode array overlaid on a photo of a skin wound on a rat model formed by surgically excising the tissue.

Figure 10B:
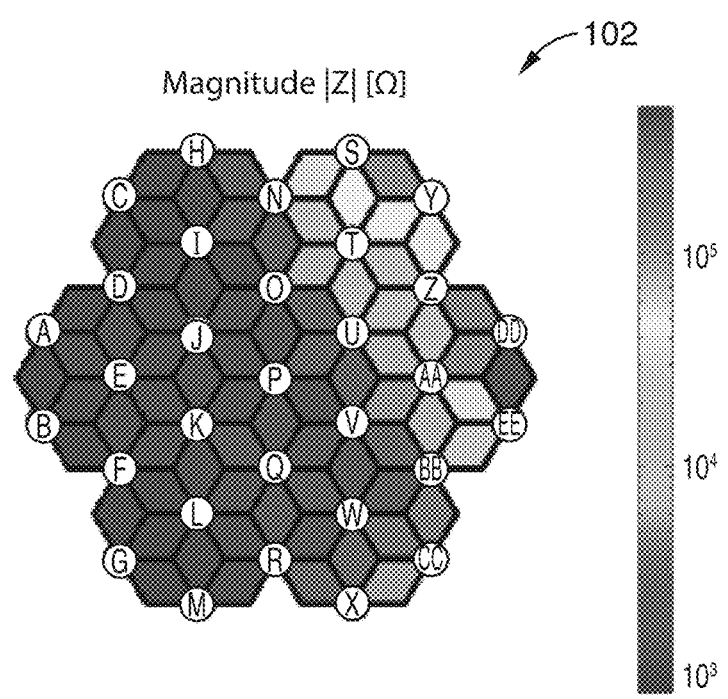
Figure 10C:
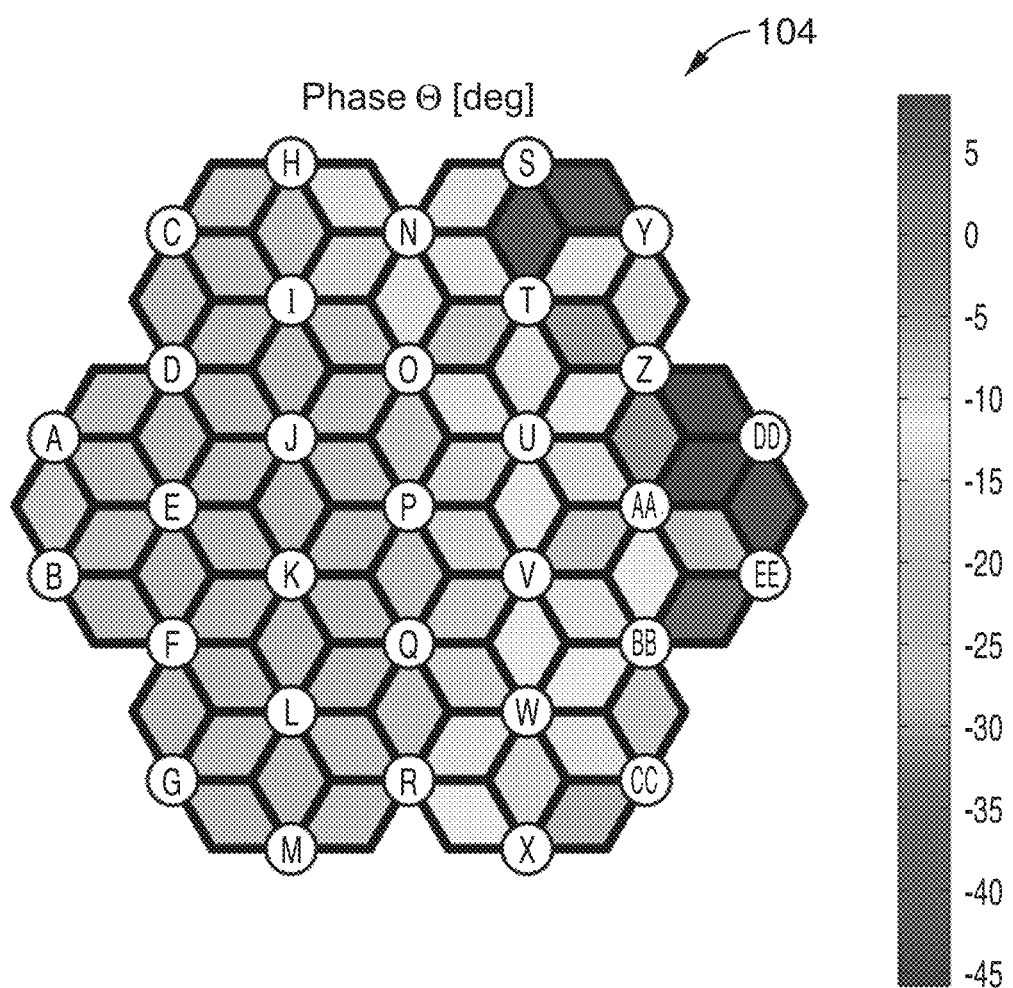

FIB. 10B and FIG. 10C show exemplary impedance maps for the wound of FIG. 10A.

Figure 11A:
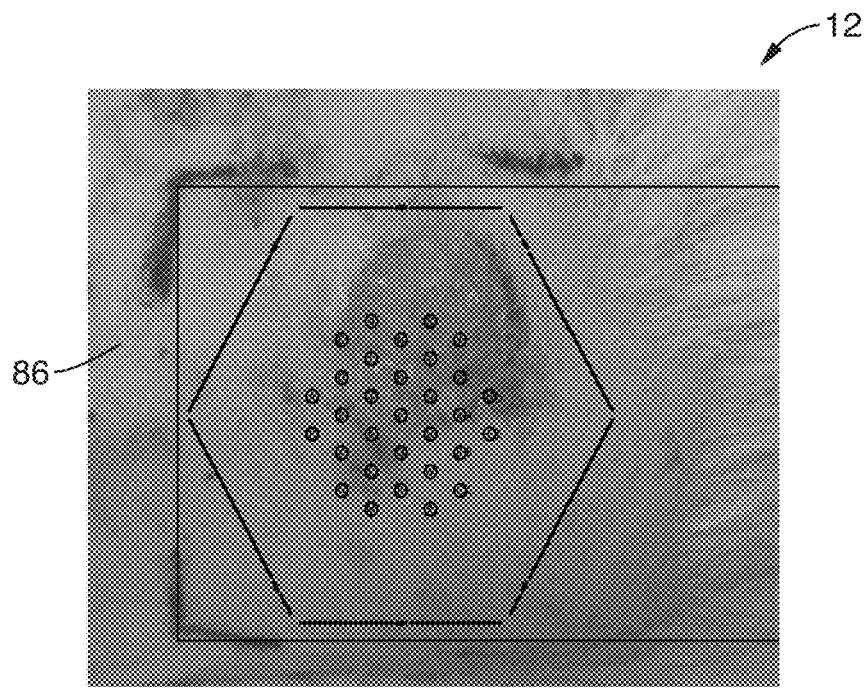

FIG. 11A illustrates an electrode array overlaid on a photo of a pressure ulcer on a rat model.

Figure 11B:
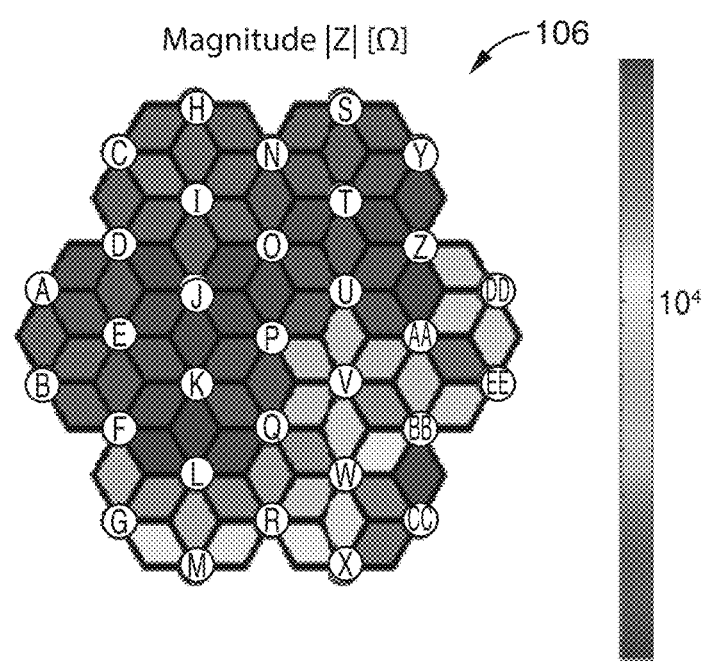
Figure 11C:
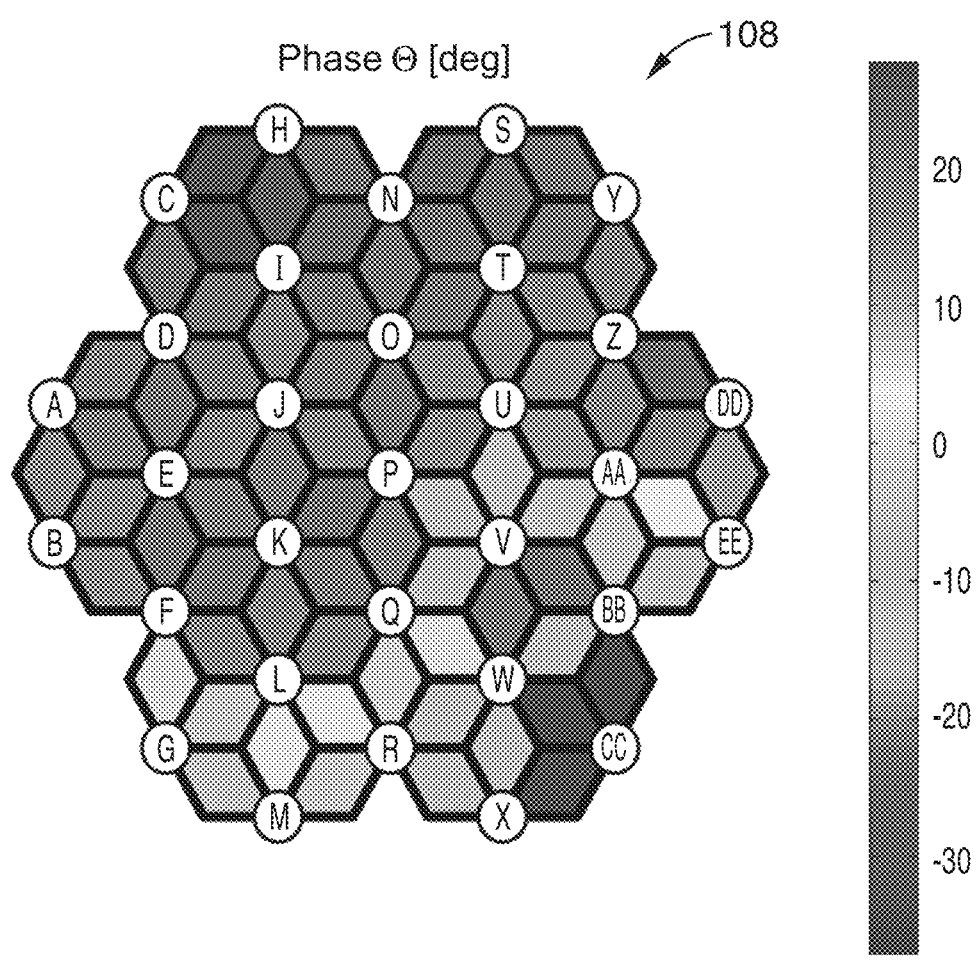
Figure 12A:
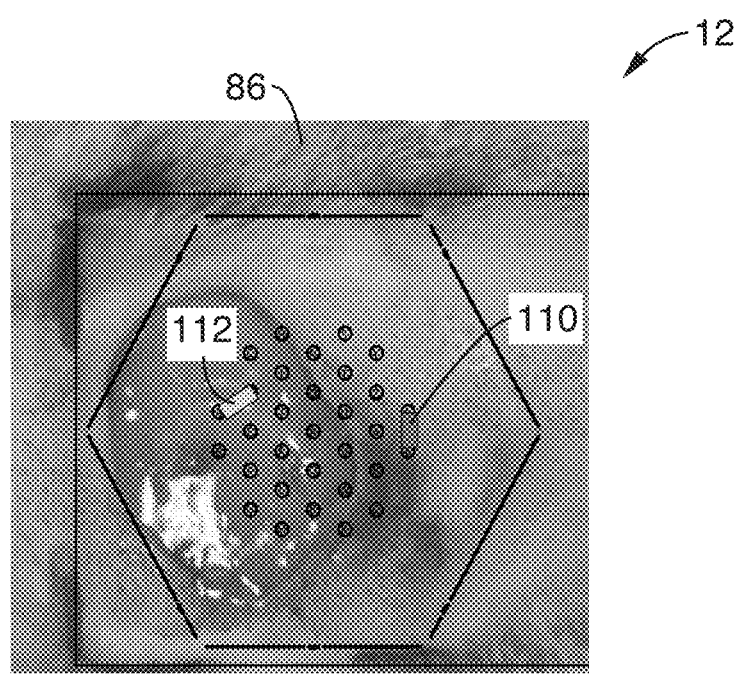
Figure 12B:
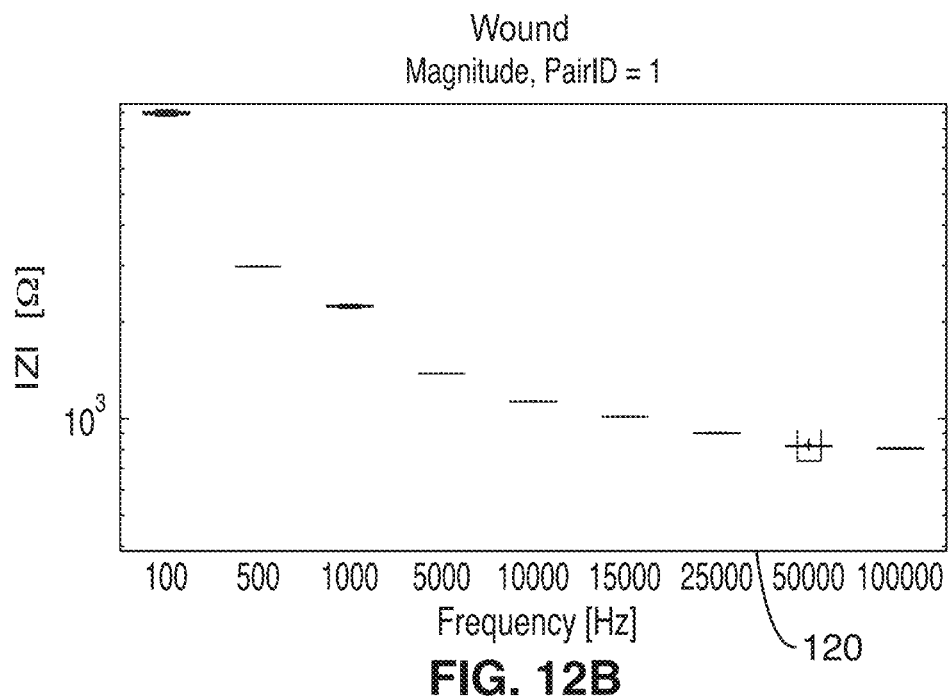
Figure 12C:
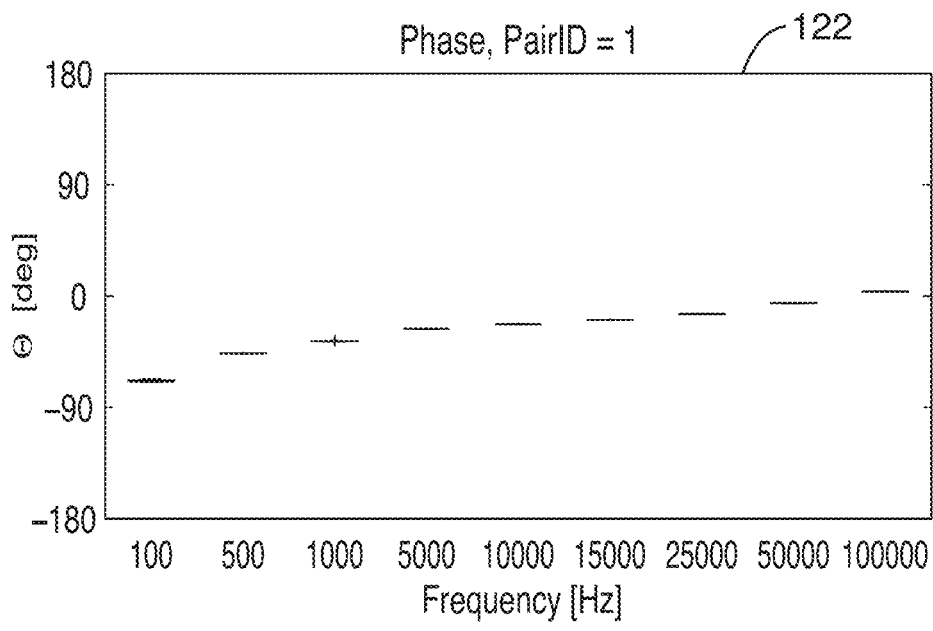
Figure 12D:
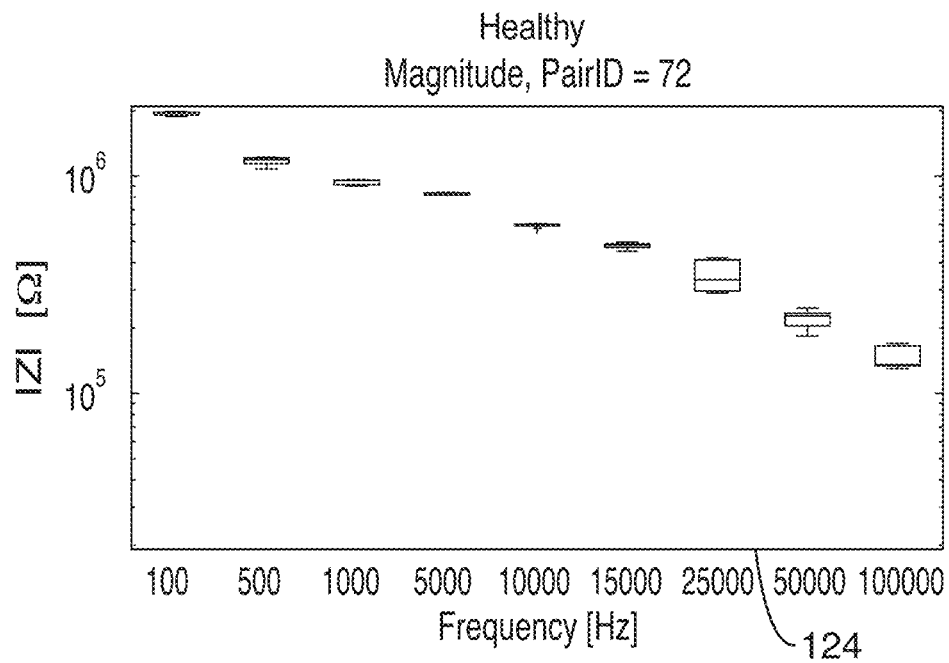
Figure 12E:
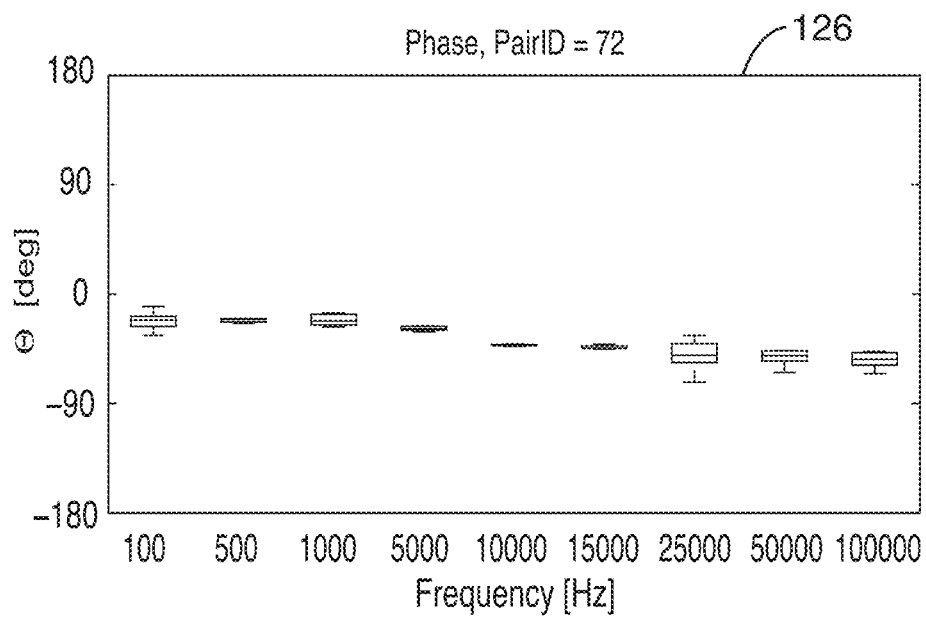
Figure 13A:
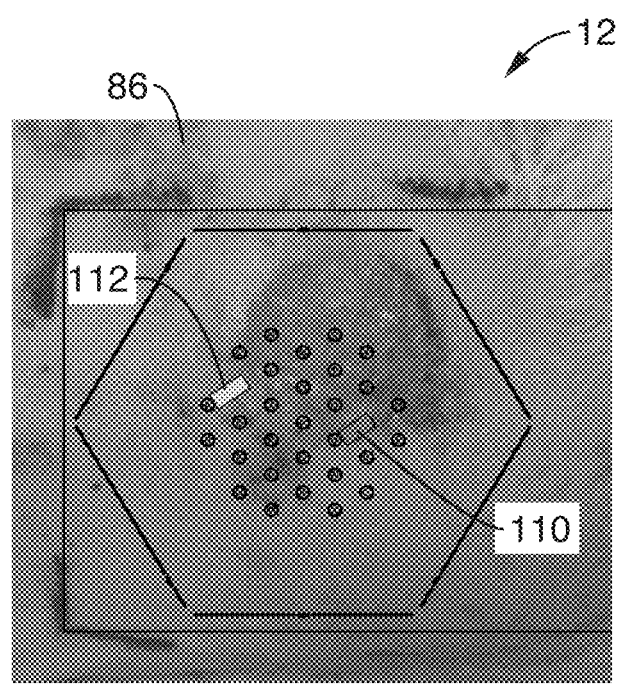
Figure 13B:
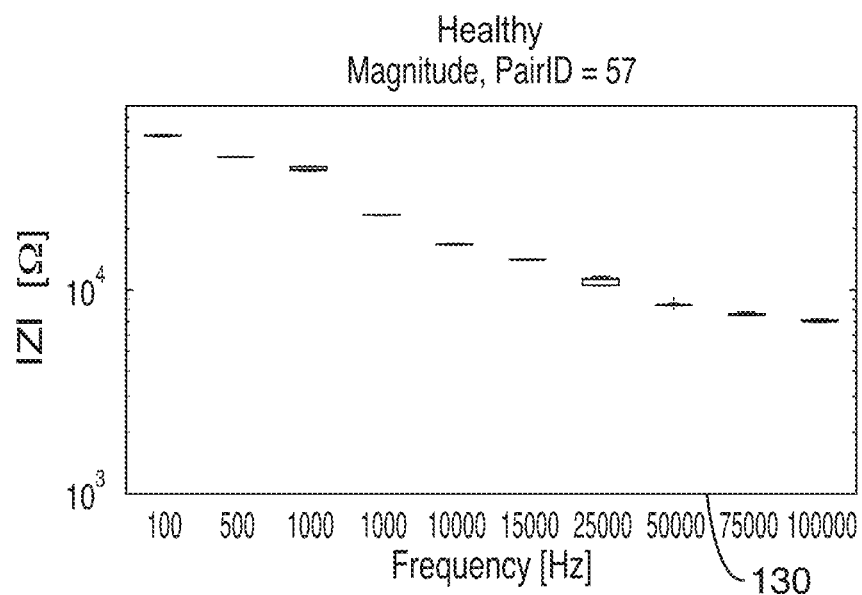
Figure 13C:
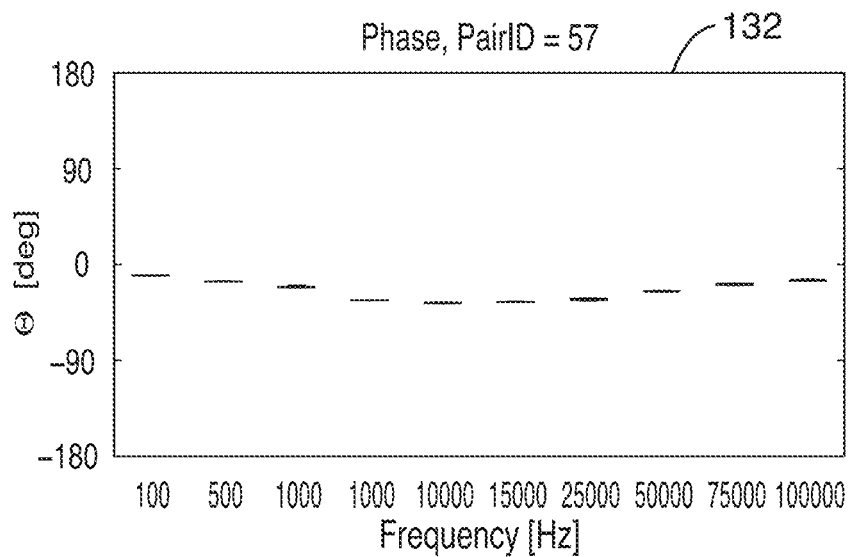
Figure 13D:
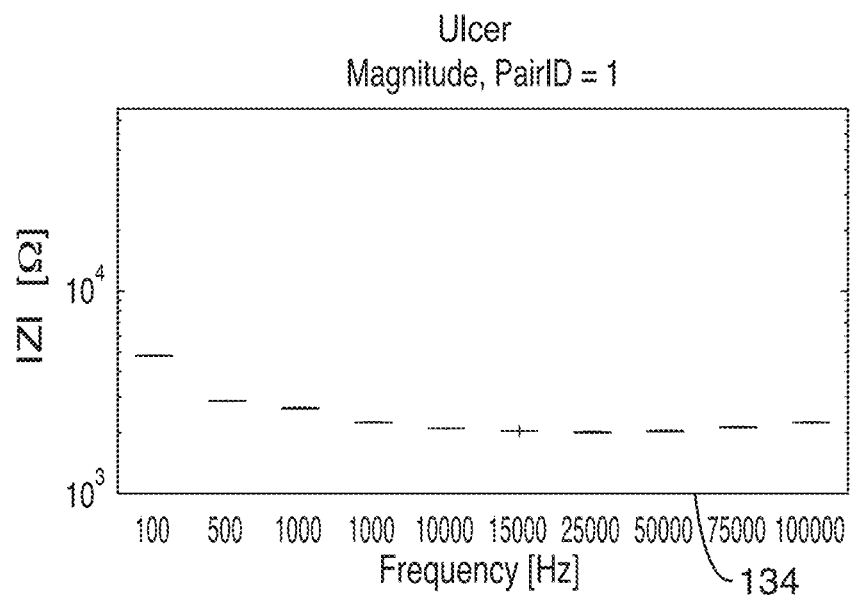
Figure 13E:
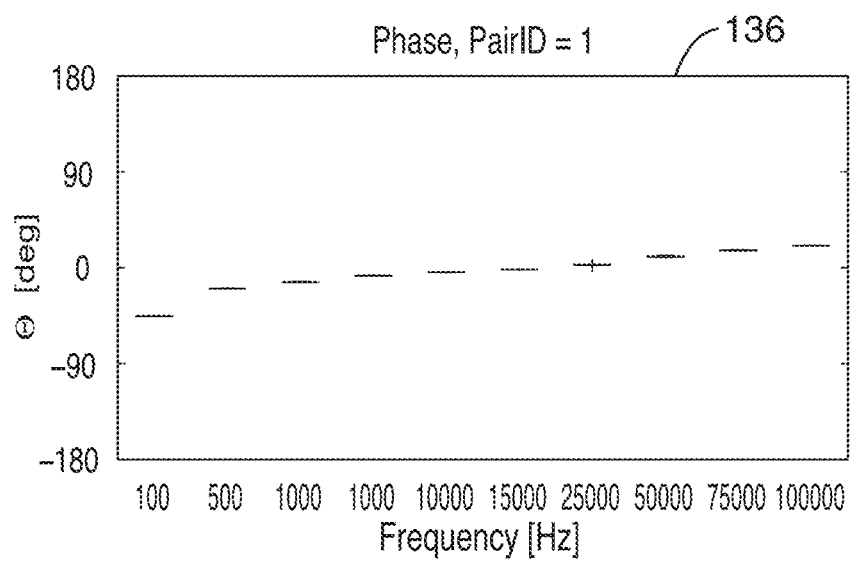

FIB. 11B and FIG. 11C show exemplary impedance maps for the wound of FIG. 11A.

FIG. 12A through FIG. 12E show further test data of the wound provided in FIG. 10A.

FIG. 13A through FIG. 13E show further test data of the wound provided in FIG. 11A.

Figure 14:
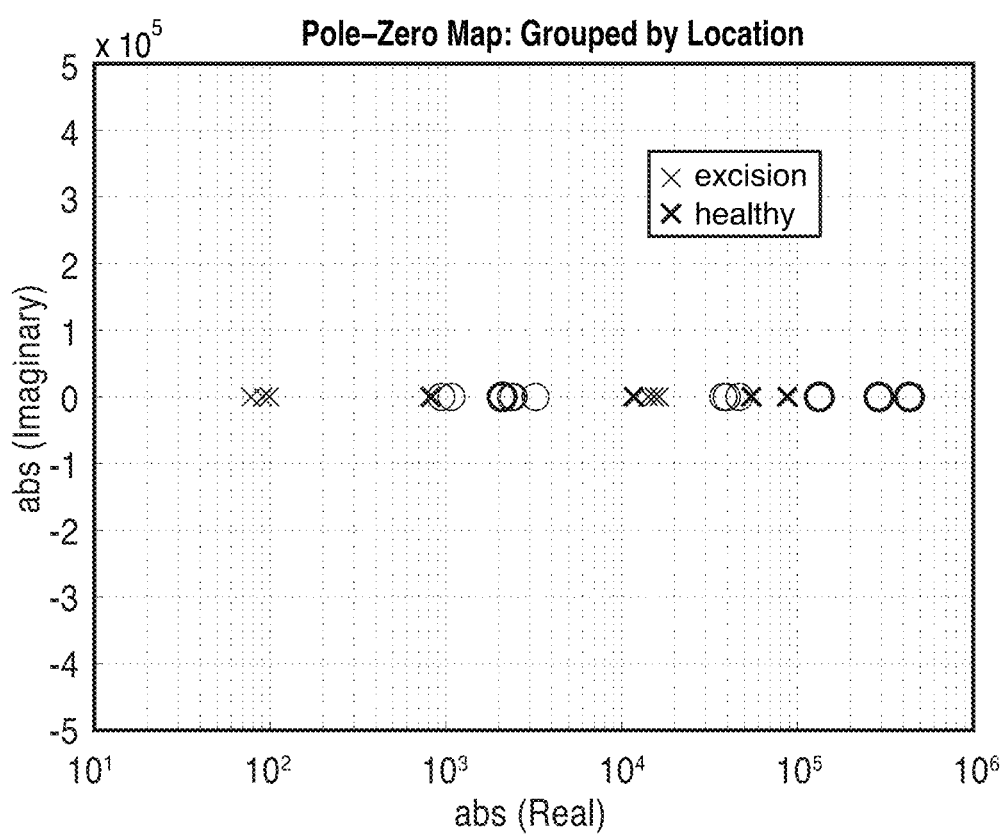

FIG. 14 shows a plot of the impedance vs frequency spectra of FIG. 13 fit to a model transfer function in containing 2 poles.

Figure 15A:
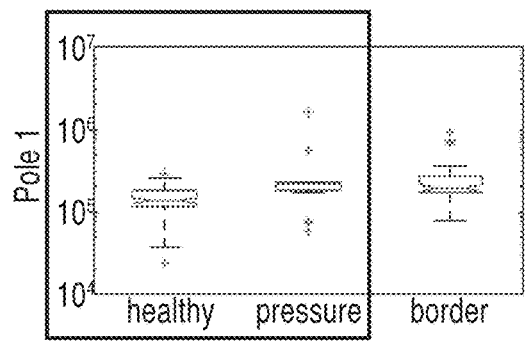

FIG. 15A shows a plot of pole 1 shown in FIG. 14.

Figure 15B:
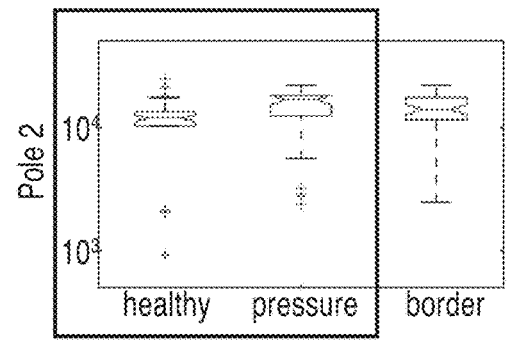

FIG. 15B shows a plot of pole 2 shown in FIG. 14.

Figure 15C:
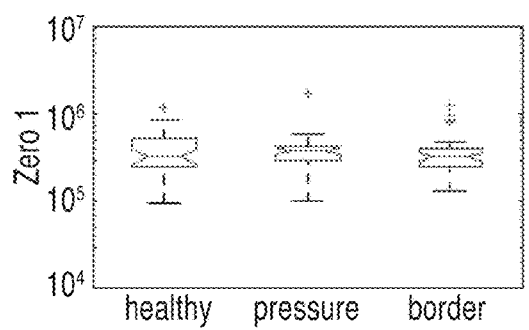

FIG. 15C shows a plot of zero 1 shown in FIG. 14.

Figure 15D:
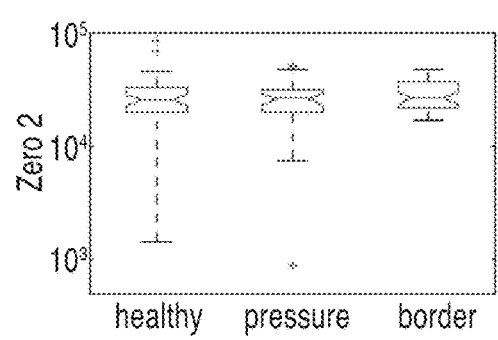

FIG. 15D shows a plot of zero 2 shown in FIG. 14.

Figure 16:
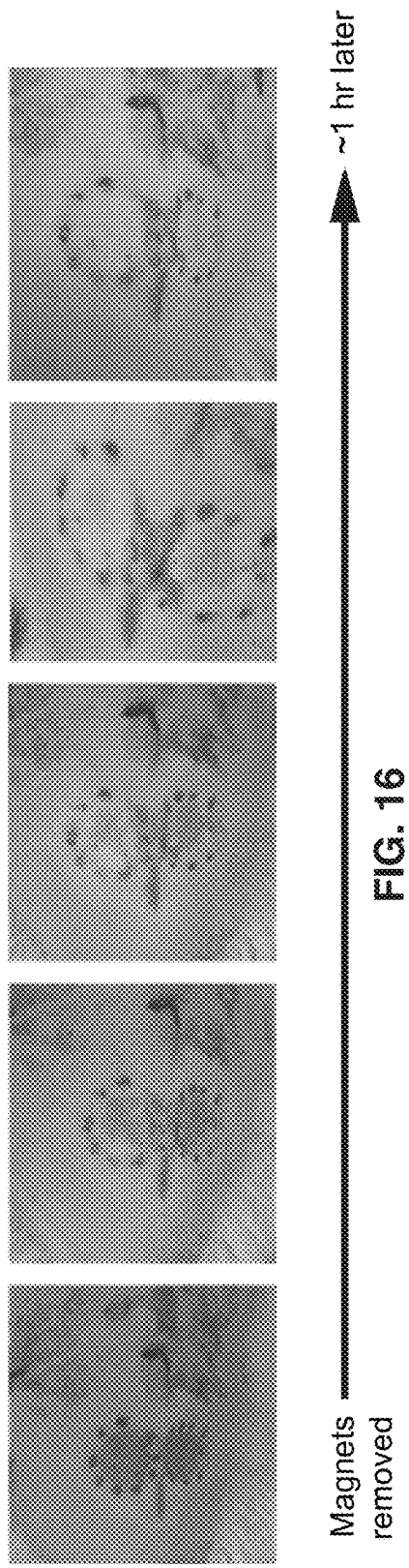

FIG. 16 shows photos illustrating the effects of magnets used to create a pressure ulcer in a rat model using a 3 hour ischemic cycle.

Figures 17A, 17B, 17C:
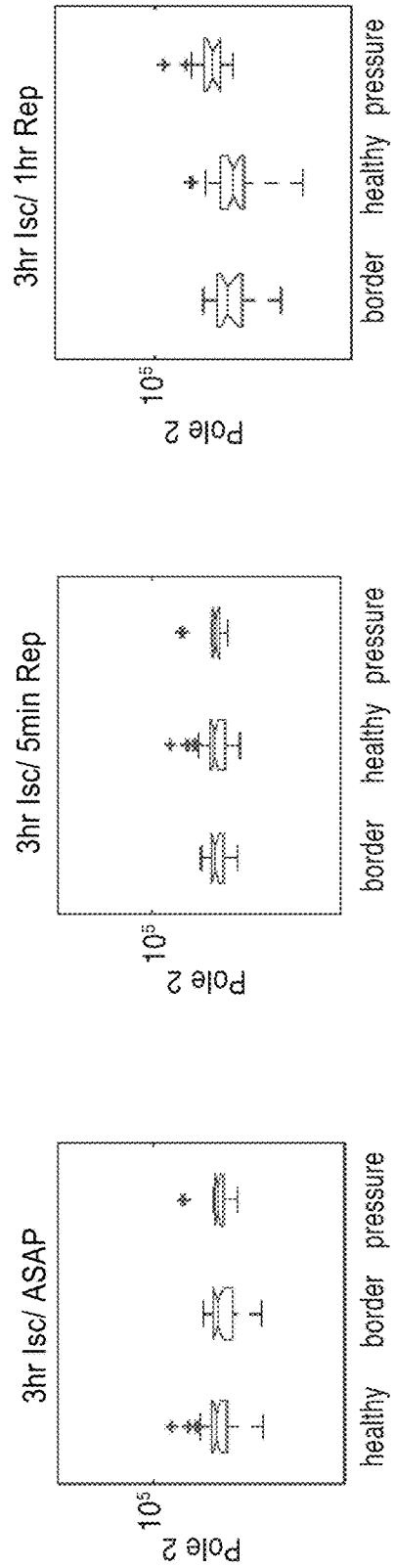

FIG. 17A through FIG. 17C show impedance measurements corresponding to the pressure ulcer of FIG. 16.

Figure 18A:
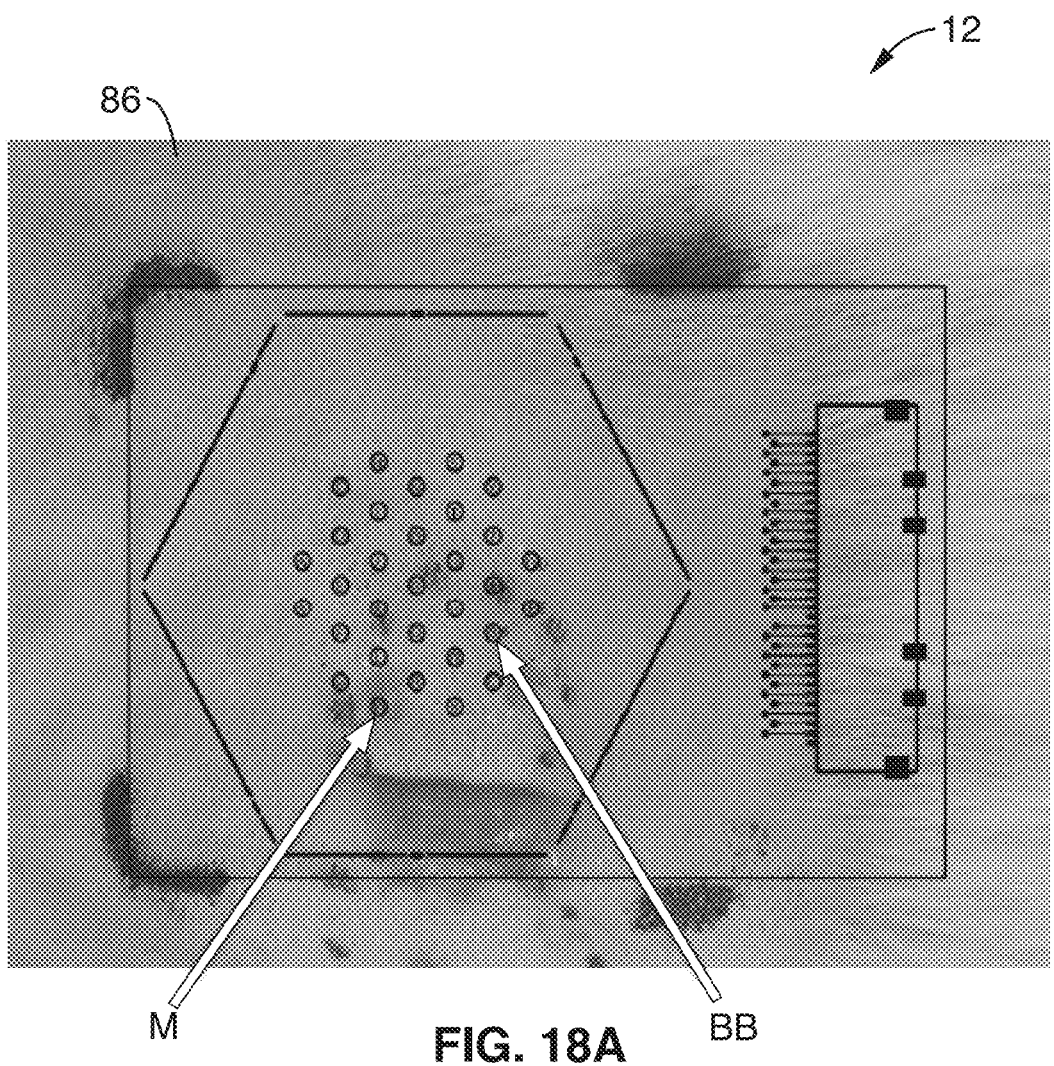
Figure 18B:
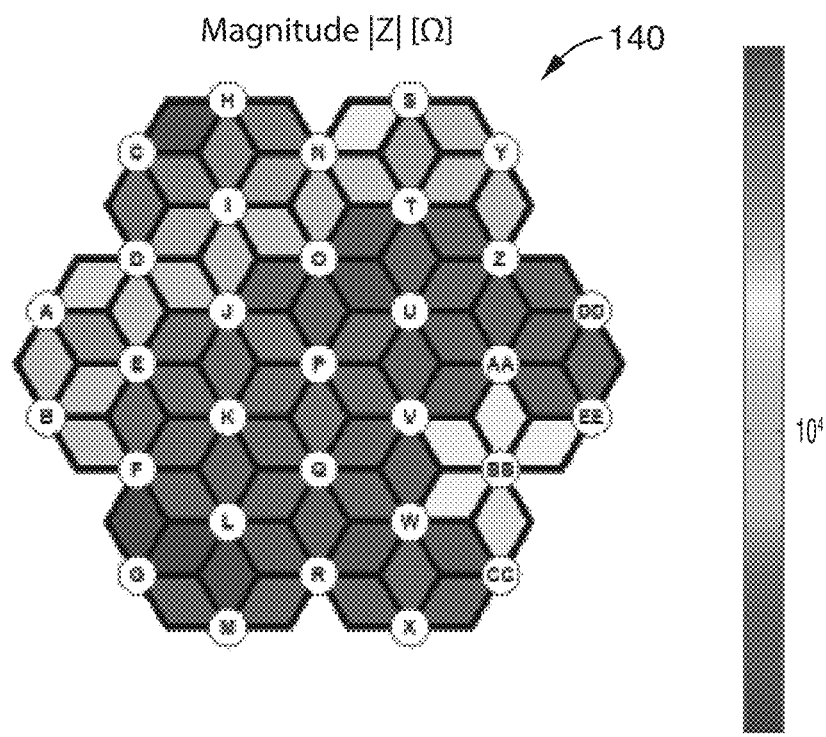
Figure 18C:
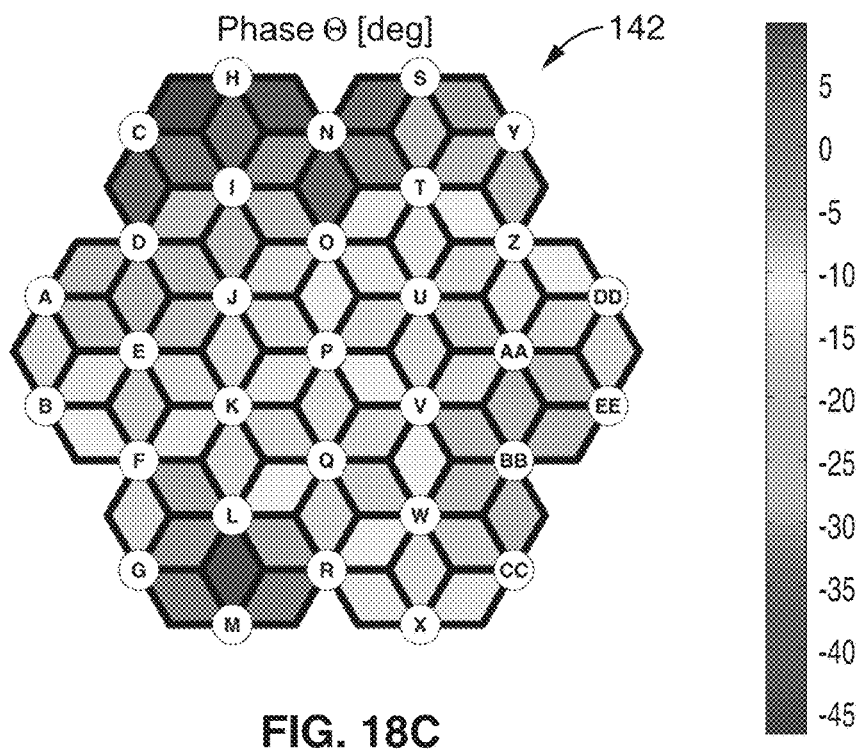

FIG. 18A through FIG. 18C illustrate the severity of pressure ulcers as a function of changing the length of time the pressure is applied.

Figure 19:
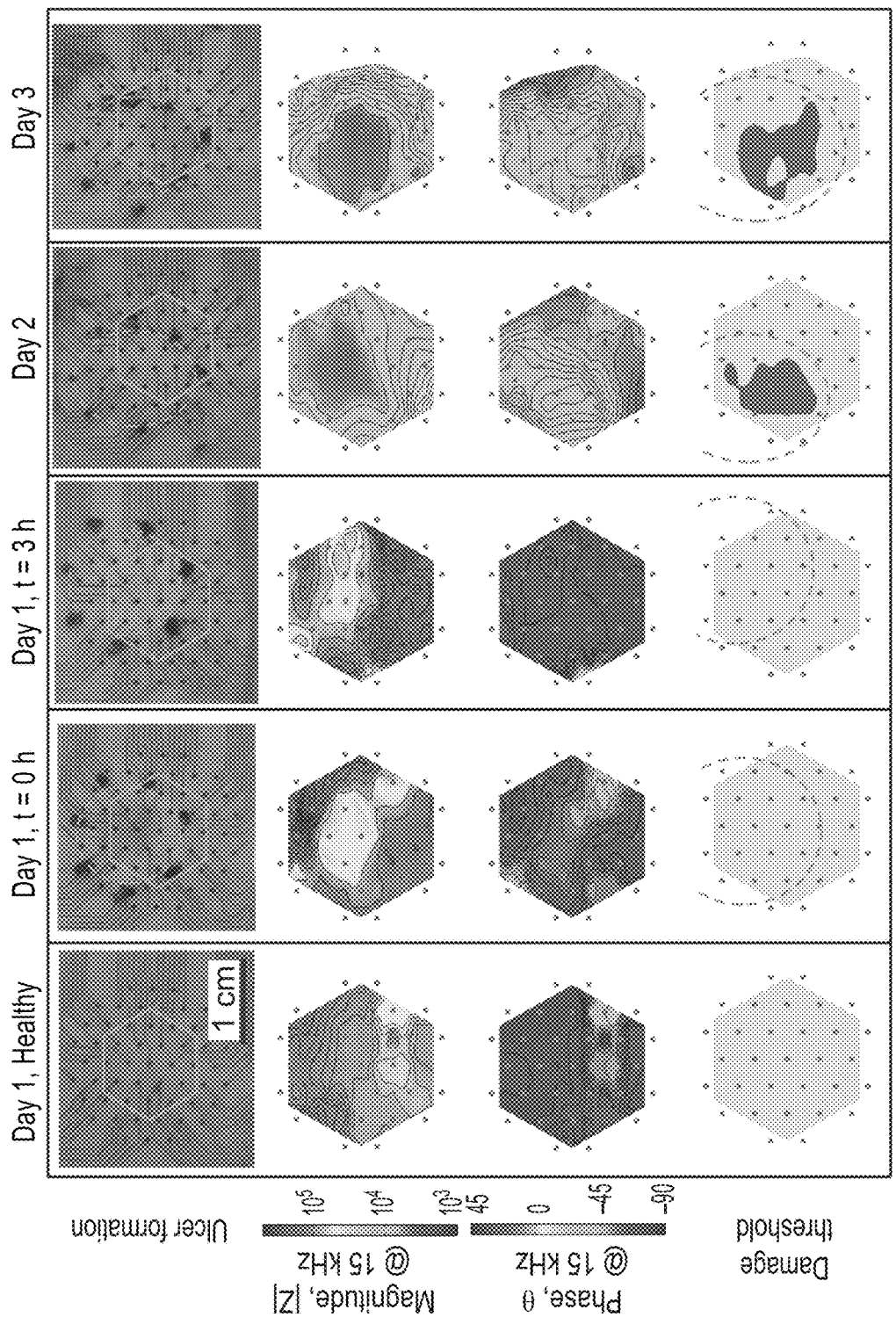

FIG. 19 illustrates the progression of a representative example of irreversible tissue damage created with a 3-hour ischemia cycle.

Figure 20A:
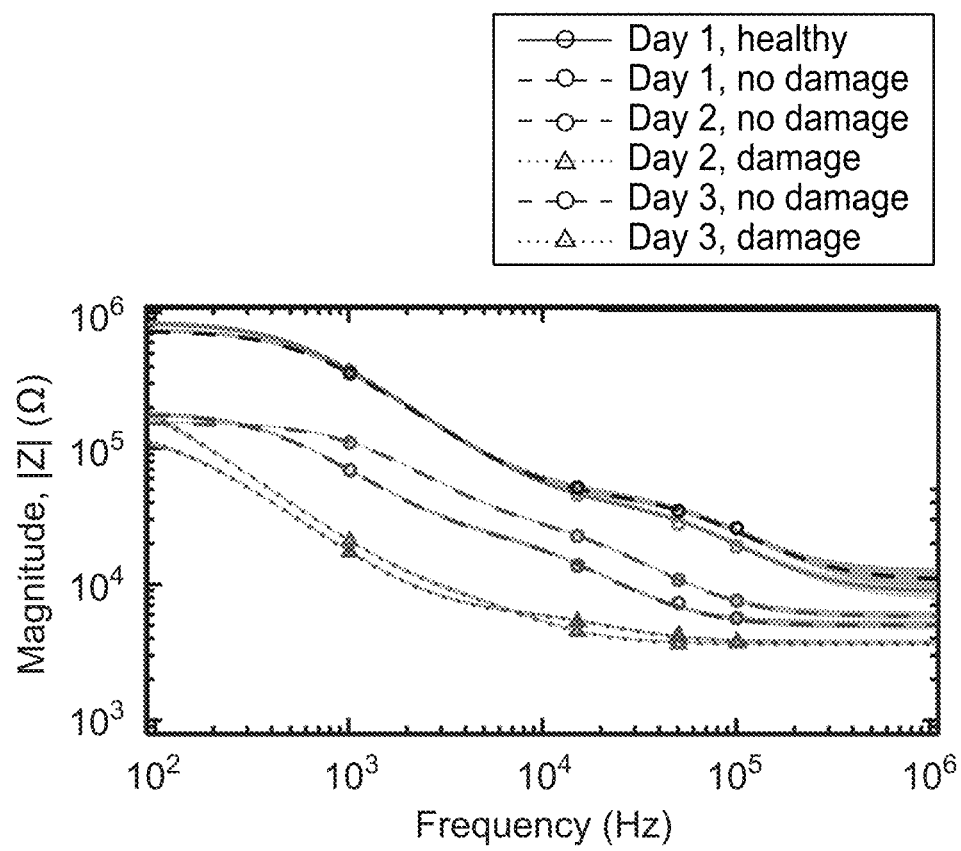
Figure 20B:
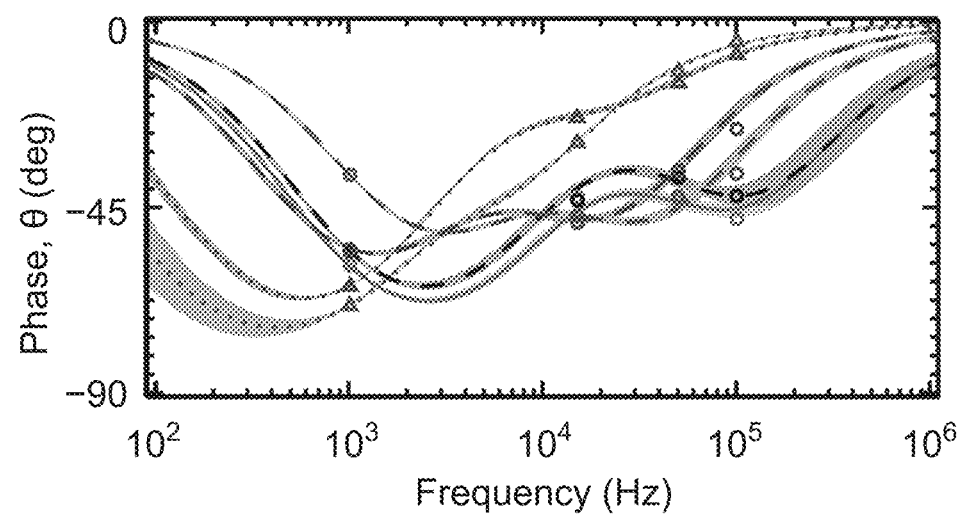

FIG. 20A and FIG. 20B show plots of impedance spectra for the wound shown in FIG. 19.

Figure 20C:
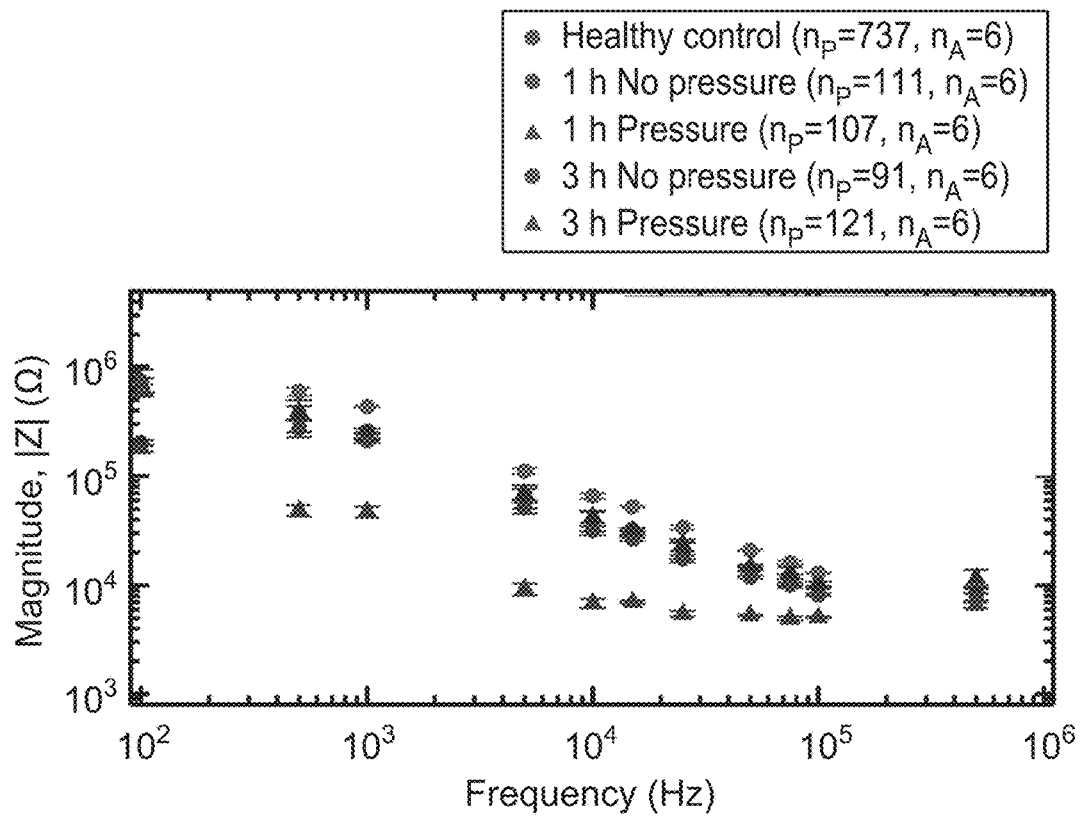
Figure 20D:
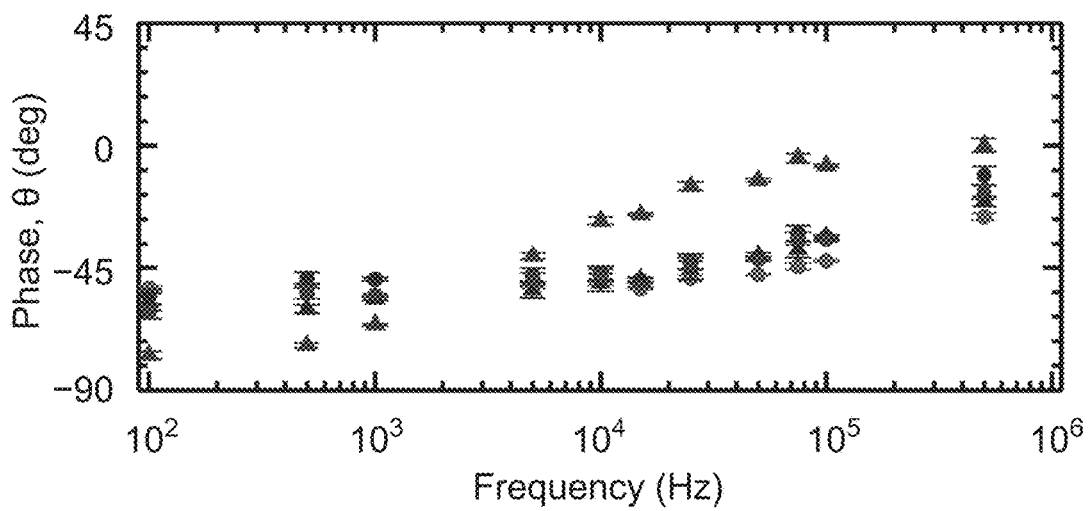

FIG. 20C and FIG. 20D show plots of impedance spectra for the wound shown in FIG. 19, averaged over all animals in the study.

Figure 21:
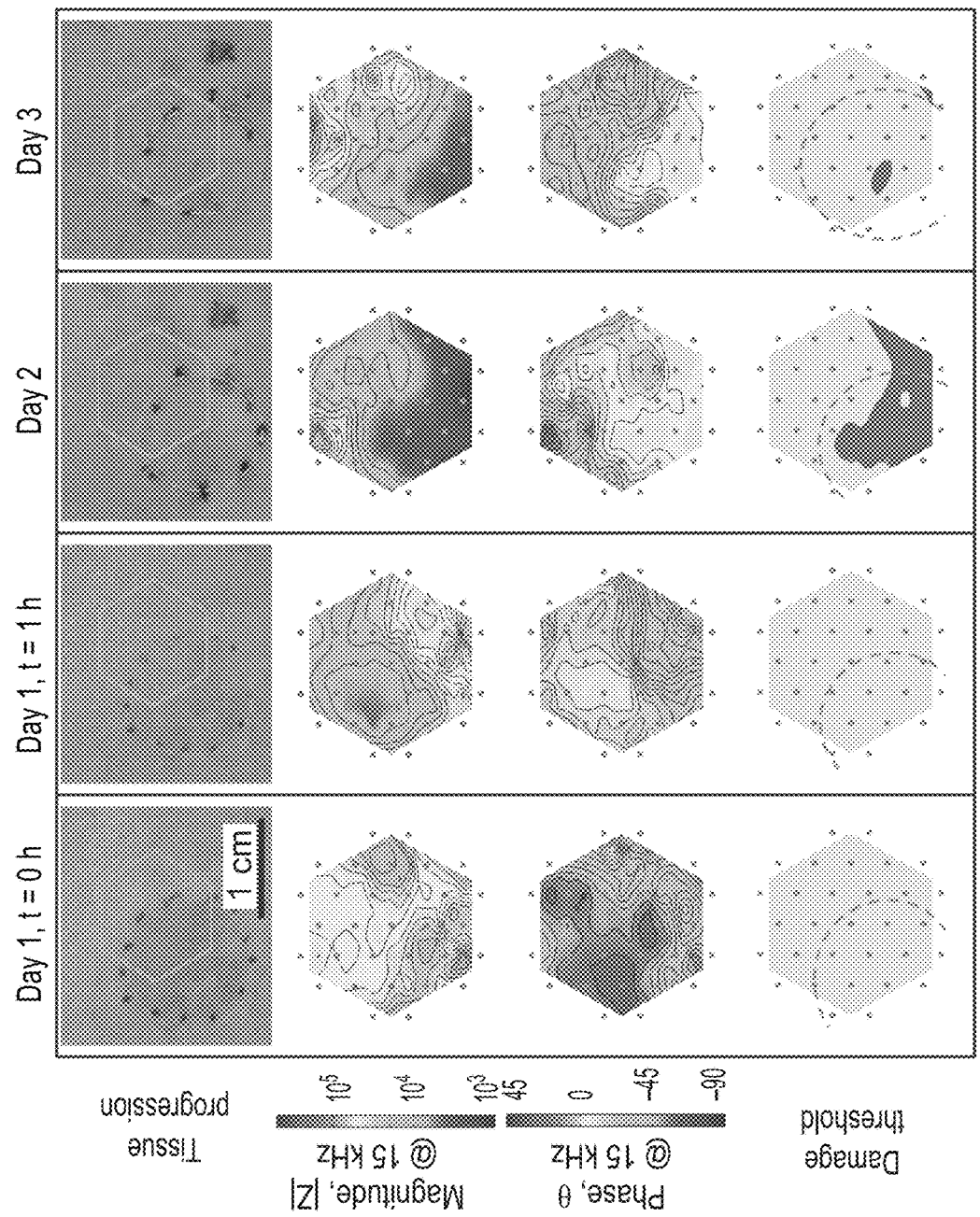

FIG. 21 shows the progression of reversible pressure damage created with a 1-h ischemia cycle.

Figure 22A:
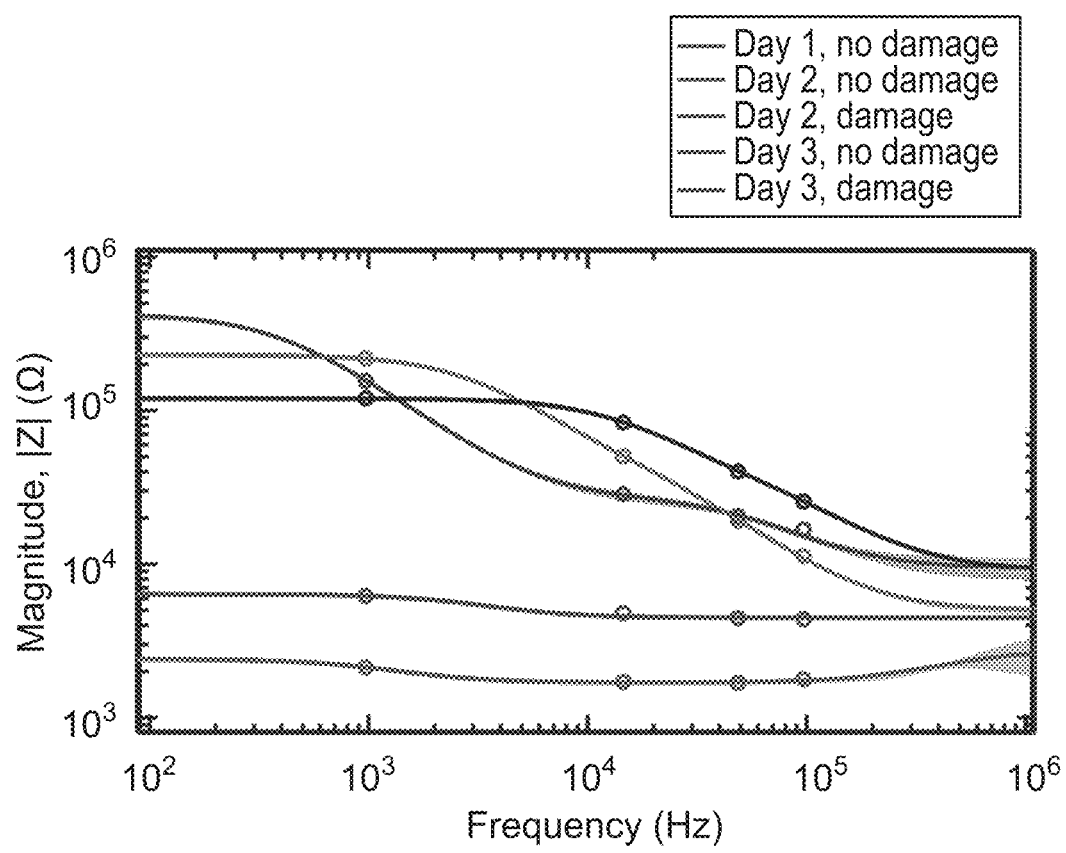
Figure 22B:
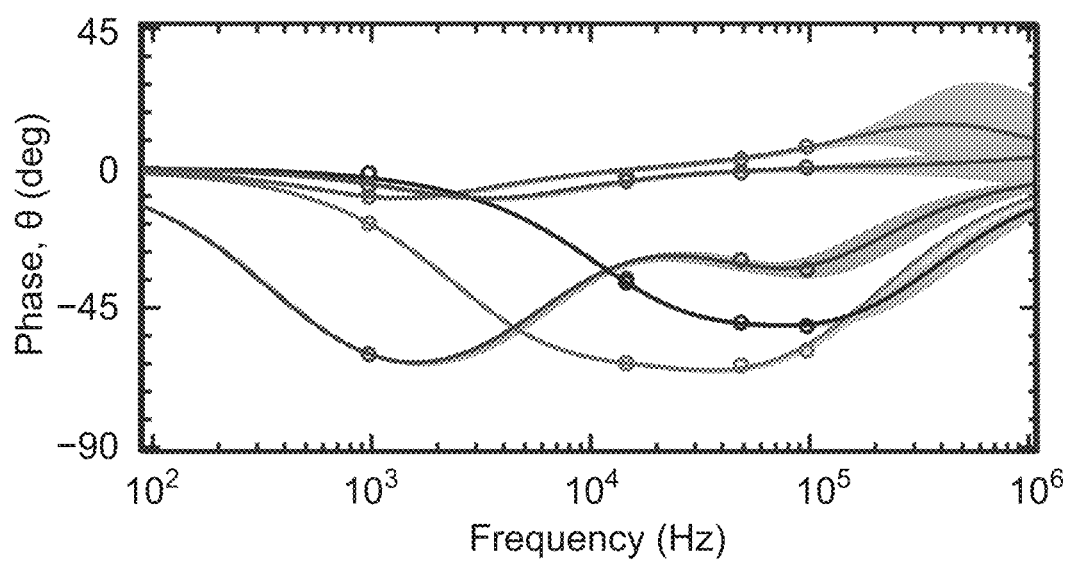

FIG. 22A and FIG. 22B show Bode diagrams showing the impedance magnitude and phase versus frequency.

Figure 23A:
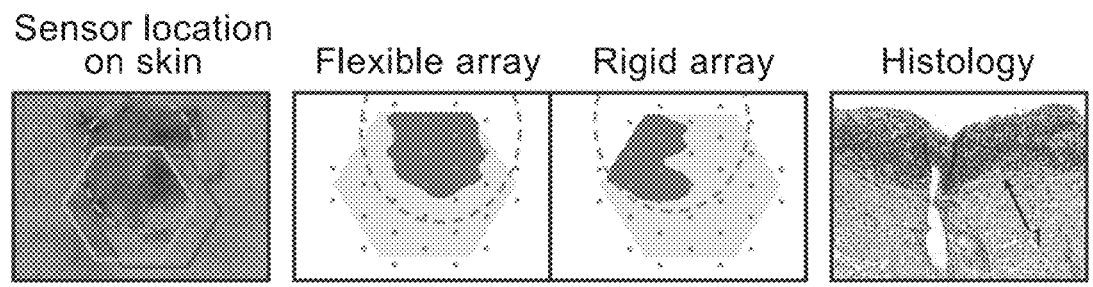
Figure 23B:
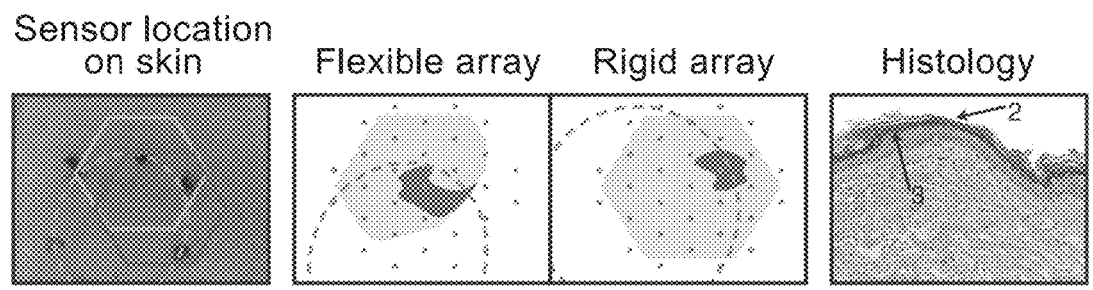
Figure 23C:
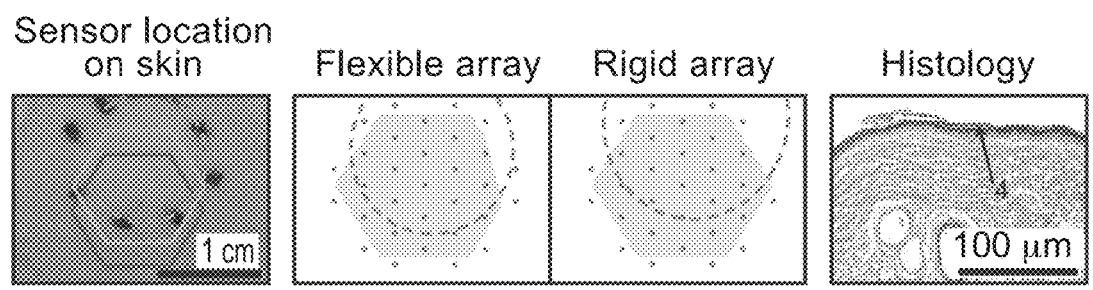

FIG. 23A through FIG. 23C illustrate early detection of pressure-induced tissue damage in a test where magnets were used to create a pressure ulcer model on rats in vivo.

Figure 24A:
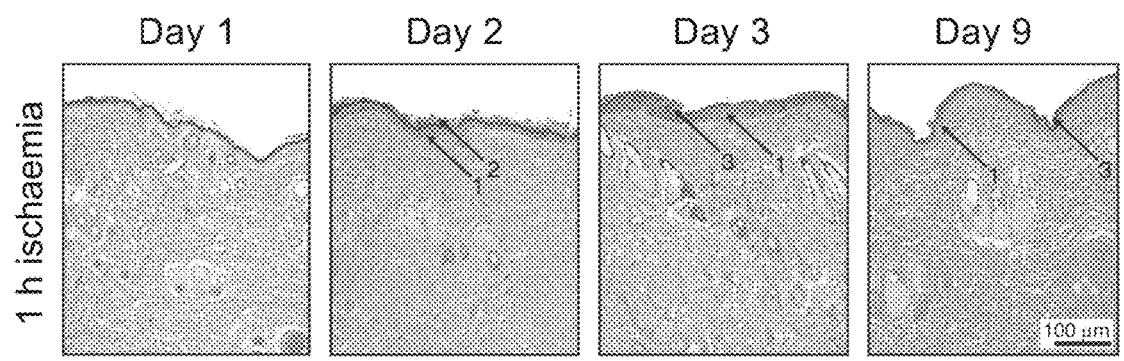
Figure 24B:
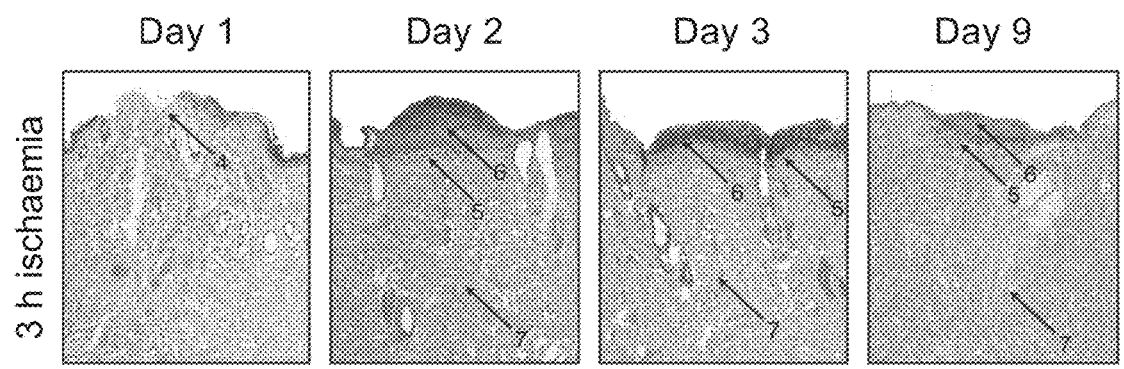

FIG. 24A and FIG. 24B show a series of images of histology of skin samples.

DETAILED DESCRIPTION

From an electrical perspective, a cell can be represented as an ion-rich conductive centre (cytoplasm) embedded in an ion-rich conductive medium (extracellular fluid), separated by a relatively non-conductive barrier (cell membrane). These ion-rich media can be described in terms of their ability to conduct charge by modeling them as resistances. Likewise, barriers to charge flow (for example, the cell membrane) can be modeled as electrical capacitances. The combination of the loss terms (that is, resistance) and energy storing terms (that is, capacitance and inductance) is known as electrical impedance. Because the impedance of a material is a function of the electrical signal being passed through it, impedances are measured across many frequencies to form a spectrum plot, which is known as impedance spectroscopy. The complex impedance Z of a medium can be expressed in polar form as:

$$Z=|Z|e^{j\theta} \qquad \text{Eq. 1}$$

with magnitude $|Z|$ and phase angle y, or in Cartesian form as:

$$Z=R+jX \qquad \text{Eq. 2}$$

with resistance R and reactance X. The reactance X represents the energy storage term. From equations (1) and (2), we see that a material with a higher capacity for energy storage (or polarization) will exhibit a larger reactance, X, and a larger phase angle, y. Resistance R is a function of both intra and extra-cellular environments of the target tissue.

Certain disturbances of the biological structures result in detectable changes in the impedance spectrum. An aspect of the present disclosure is a device that utilizes the electrical 'signature' of the cell membrane. A well-functioning cell membrane is relatively impermeable and thus behaves like a capacitor in the presence of electric current. Cell damage or death results in a loss of membrane structure and integrity, allowing ions and current to pass through the membrane. Thus, damaged cells will exhibit higher electrical conductance through the membrane and less capacity to store charge. In other words, the cell behaves less like a capacitor and more like a resistor. In an impedance measurement, this manifests itself as a phase angle y closer to zero (or equivalently, a smaller reactance, X). Thus, a premise of the present disclosure is that pressure ulcers may be detected and diagnosed based on the changes in electrical impedance caused by the loss of cellular integrity or cell death following an ischemia/reperfusion event.

Figure 1:
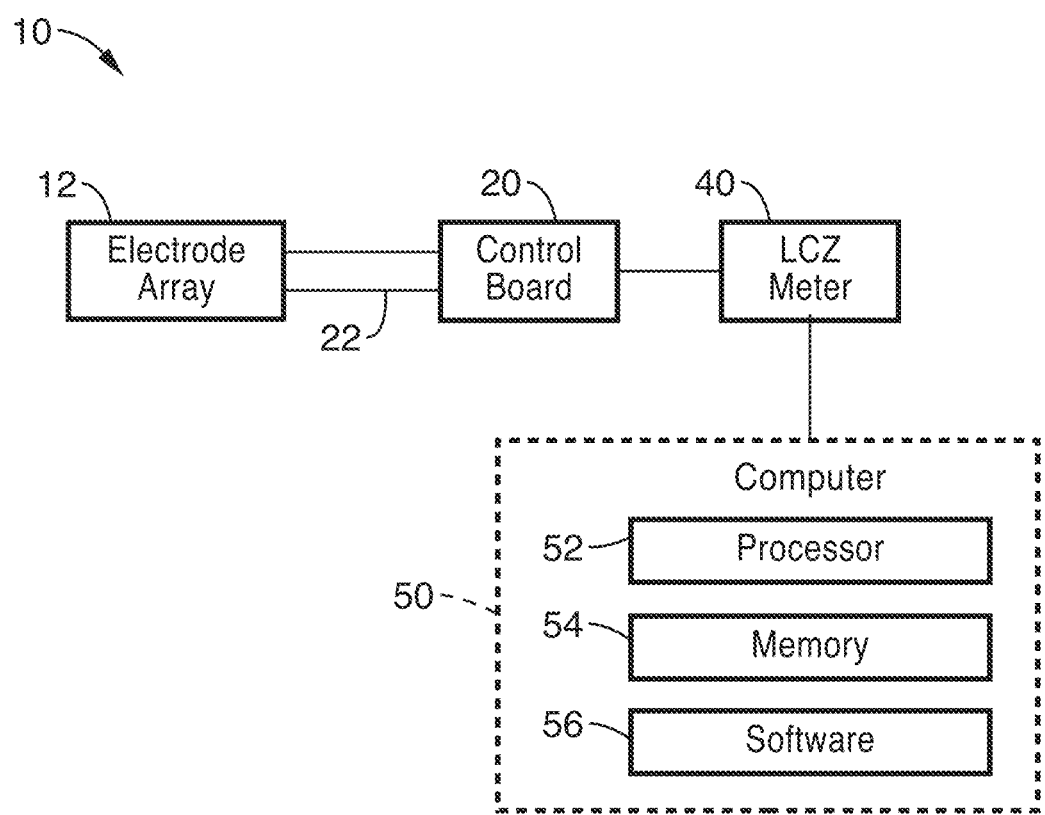
FIG. 1 shows a schematic view of a sensing system for analysis of skin wounds using impedance spectroscopy in accordance with the present description.

FIG. 1 shows a schematic view of a SMART (Sensing, Monitoring, And Real-Time) sensing system 10 for analysis of skin wounds using impedance spectroscopy in accordance with the present description. SMART sensing system 10 is preferably implemented as a flexible bandage utilizing impedance spectroscopy to detect, for example, changes in biological tissue structures signaling (1) the formation of pressure ulcers, and/or (2) wound healing. When used in vivo, impedance spectroscopy using sensing system 10 may detect subtle changes in the subject tissue, enabling objective assessment and providing a unique insight into the condition of a wound.

The sensing system 10 primarily comprises two primary components: (1) a control board 10 comprising the electronic components (microcontroller, multiplexers, etc.), and (2) an electrode array 12 that contacts the skin/wound and from which impedance measurements are taken.

By way of example, and not of limitation, the array 12 of electrodes 14 (see FIG. 4) is used to create a visually intuitive map of electrical impedance. A plurality of multiplexers 24a through 24e (FIG. 2) allow for specific selection of drive and sense electrodes in the array 12, and the output of these multiplexers is controlled by a control board 20. The electrode array 12 is connected through the control board 20 to an impedance analyzer 40 (e.g. LCZ meter, or the like) which provides the drive signal and calculates the complex impedance of the tissue. Impedance is measured at various frequencies, and any dispersion observed in the frequency response is analyzed. The control board 20 configuration also has the capability of providing electrical stimulation to specific sites on a wound with the potential to increase the rate of wound closure.

Output from the impedance analyzer 40 is preferably coupled to a computer 50 comprising application software 56 for analyzing the frequency response of the tissue. The application software 56 is stored in memory 54 and executable on processor 52.

Control board 20 comprises a microcontroller 30 that dictates the measurement configuration (e.g. 2-point or 4-point impedance, as described in further detail below), as well as which electrodes are used as the sense pair (S+ and S−) and the corresponding drive pair (D+ and D−). The software code 56 for microcontroller 30 code is configured to cycle through all possible nearest-neighbor pairs to generate a map of the measured impedance.

The impedance analyzer 40 may be connected to computer 50 via USB or like connection (not shown). In one embodiment, data (impedance magnitude and phase) is collected from array 12 at a rate on the order of 5-10 data points per second. A signal is sent from the control board 20 to the computer 50 to indicate that a pair of electrodes 14 is ready to measure, and then the computer 50 sends a trigger to the impedance analyzer 40 to measure the impedance. Typically, each nearest-neighbor pair is measured for 2-3 seconds, which allows all electrode pairs in the array 12 to be measured (at a single frequency) in less than 5 minutes.

In the embodiment shown in FIG. 1, the electrode array 12 is on a separate board than the control board 20, allowing only the electrode array board 12 to come in contact with the skin/wound while positioning the control board 20 farther away from the patient. In this configuration, a flexible cable 22 may be used to electrically connect the array 12 with the control board. In one embodiment, cable 22 may comprise flat flexible cables (FFC) used to connect the flexible electrode array 12 to the control board 20. The FFC can either be bonded with anisotropic conductive film (ACF) directly to printed pads 26 on the flexible substrate 18 (see FIG. 4), or a mating FFC connector can be attached to the flexible circuit 26.

Additional configurations are contemplated. For example, both the electrode array 12 and control board 20 may be constructed to have the same size/footprint so they can be stacked on top of one another (not shown). In such configuration, aligned vias on both boards can be electrically connected using solder paste or by threading with thin, conductive wire.

Figure 2:
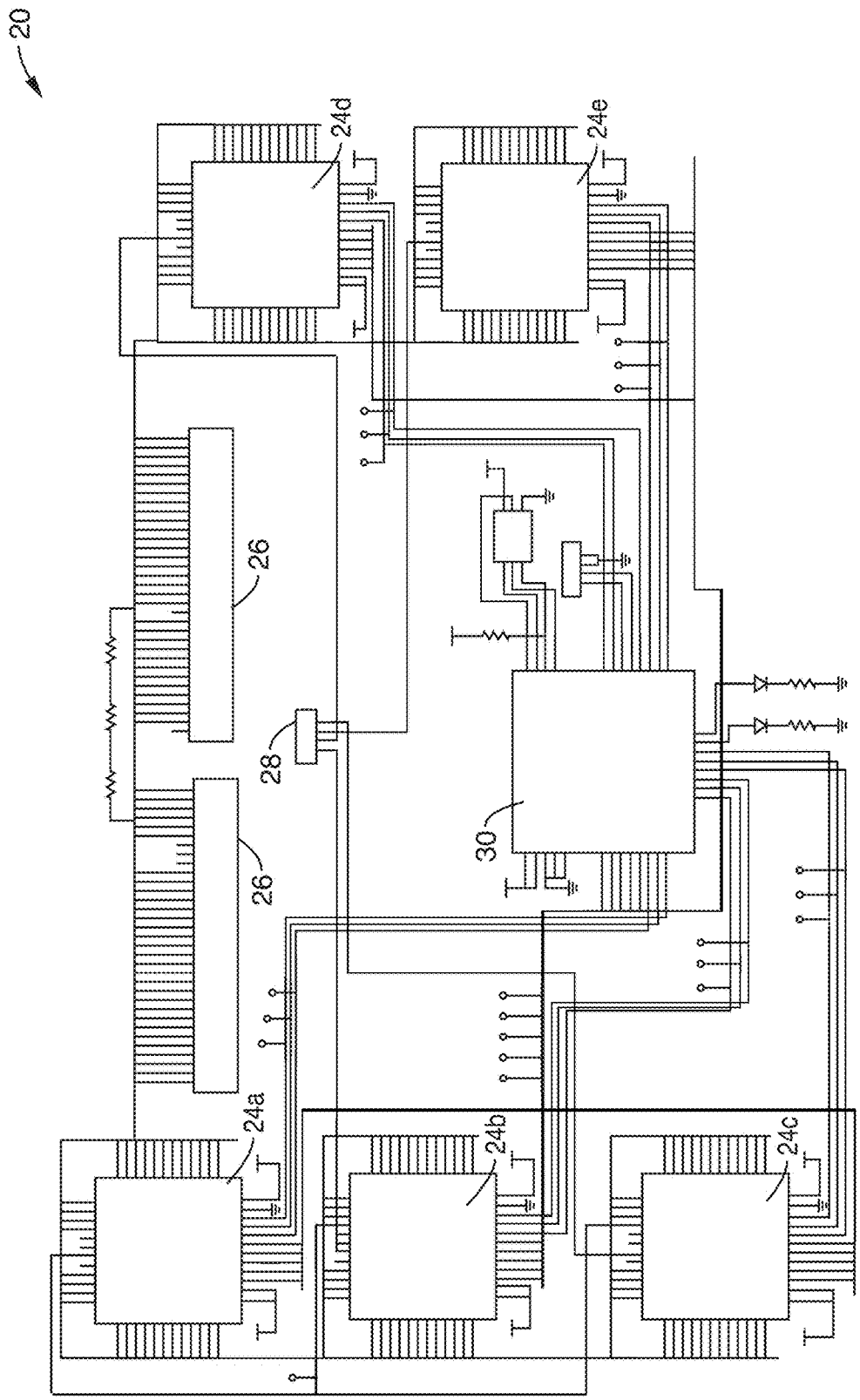
FIG. 2 illustrates schematic circuit diagram of an exemplary control board.
Figure 3:
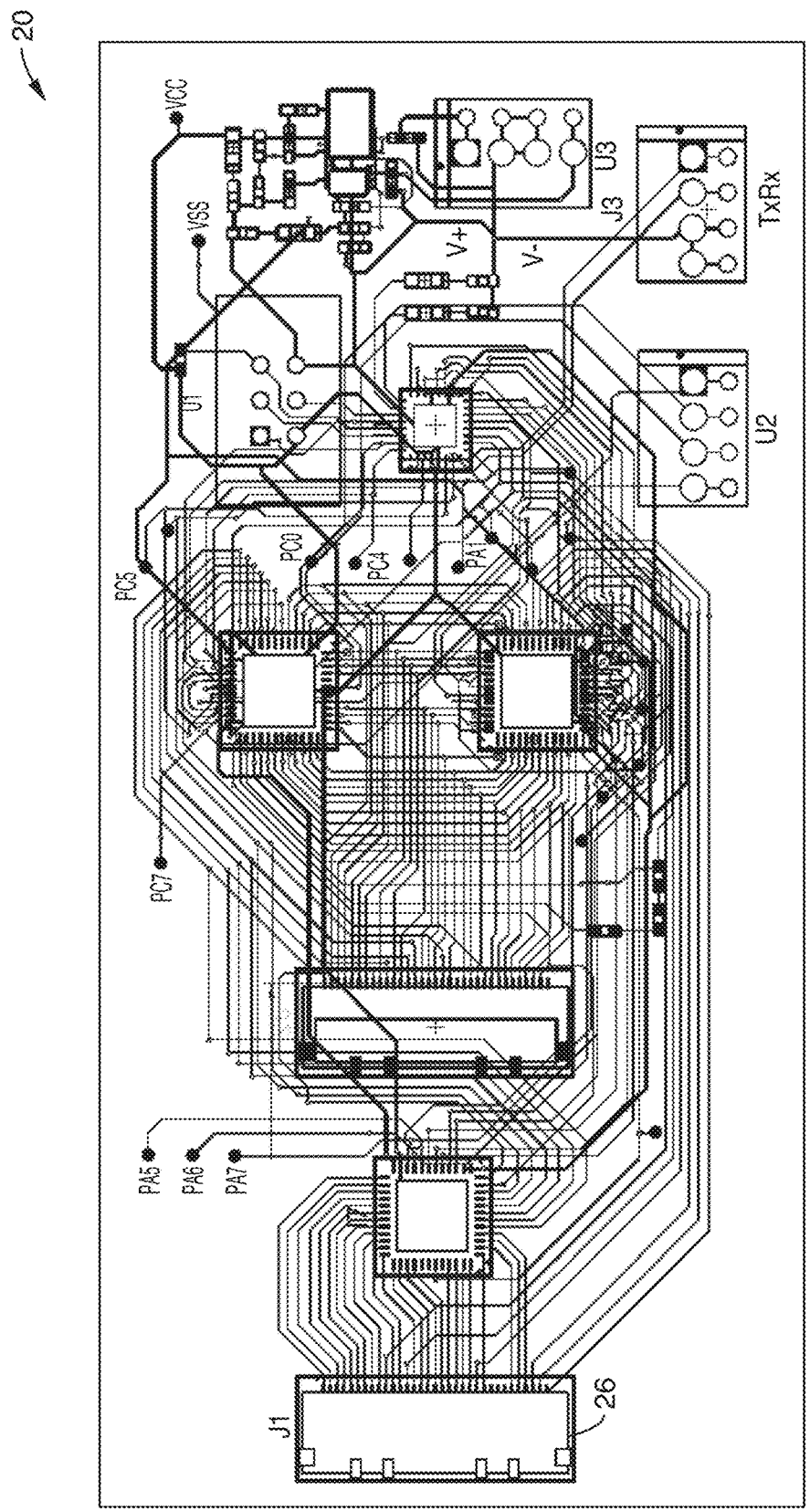
FIG. 3 illustrates a circuit layout diagram of the control board of FIG. 2.

FIG. 2 illustrates schematic circuit diagram of an exemplary control board 20, while FIG. 3 illustrates a circuit layout diagram of control board 20. In one exemplary configuration, control board 20 may comprise a microcontroller/processor 30 (e.g. ATTiny 828) coupled to a plurality of multiplexers 24a through 24e (e.g. ADG732 MUX), a programming port, LCZ connector 28, a pair of voltage regulators (e.g. supplying +/−3V) and connectors 32 to electrode array board 12. The board 20 may be powered by a mobile power source (e.g. four AA batteries).

Figure 4:
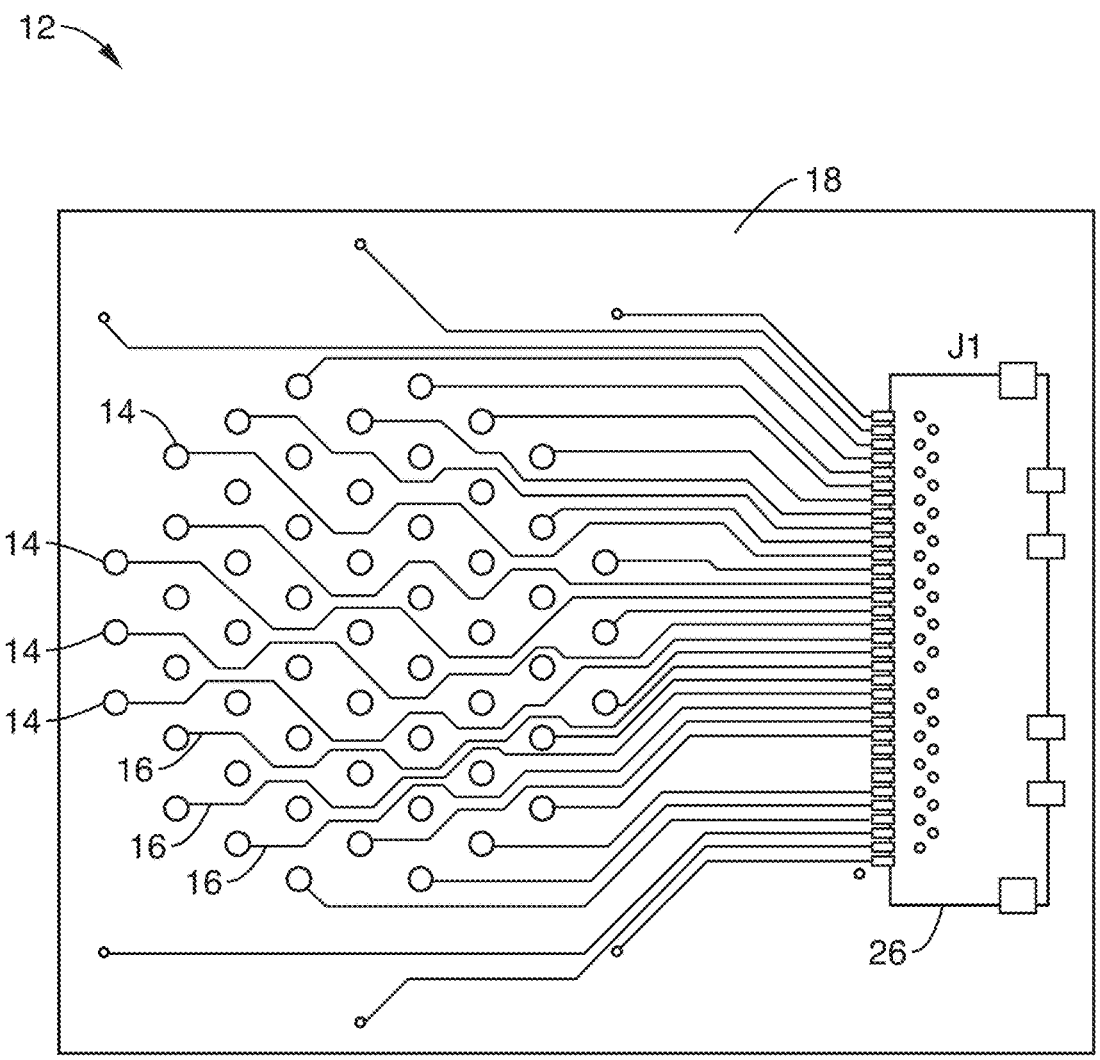
FIG. 4 shows a plan view of an exemplary electrode array board disposed on a conforming flexible substrate in accordance with the present description.

FIG. 4 shows a plan view of an exemplary electrode array board 12 disposed on a thin (e.g. 35 μm) conforming flexible substrate 18 in accordance with the present description. The array of electrodes 14 array and routing layers are preferably inkjet printed using commercial inks formulated with gold nanoparticles. Conductive Au traces 16 may be deposited in a layout coupling connector 26 and electrodes 14 as shown in FIG. 4, which is configured to comply with criteria for Au inkjet printing on the selected substrate 18 (e.g. minimum line-width and interline spacing of 50 μm). Exemplary materials for flexible substrate 18 include parylene, polyethylene naphthalate (PEN), polyimide (Kapton) or like materials. The gold nanoparticles for electrodes 14 and traces 16 are generally sintered at temperatures higher than the melting temperature of the substrate 18, so lower temperature and longer times were used to make the printing compatible with selected substrates.

Inkjet printing of conductive metal ink onto flexible plastic substrates provides a fast, inexpensive fabrication method that can be changed on-the-fly as the design evolves.

Figure 5A:
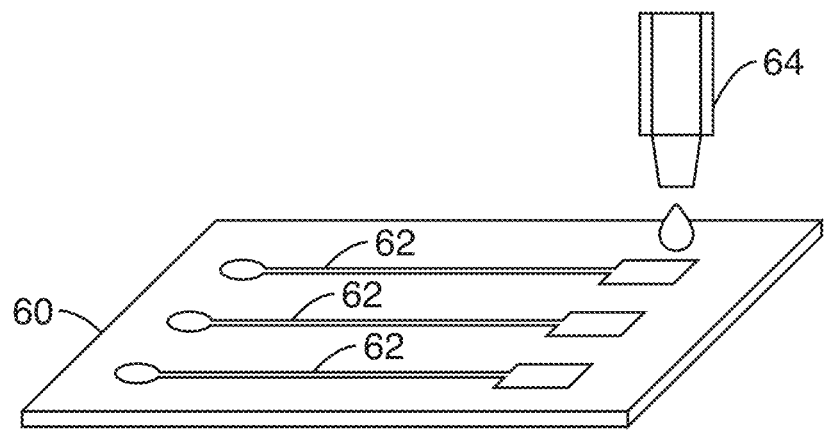
FIG. 5A through FIG. 5E illustrate a fabrication process for the printed flexible electrode array of FIG. 1.
Figure 5B:
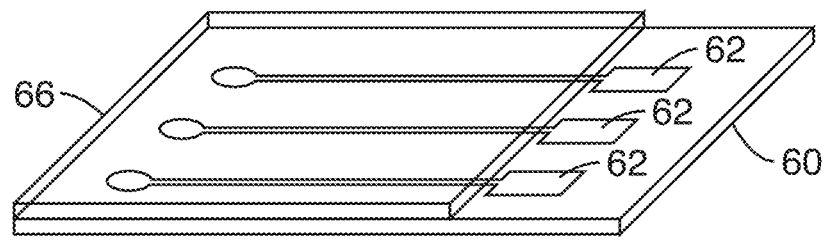
Figure 5C:
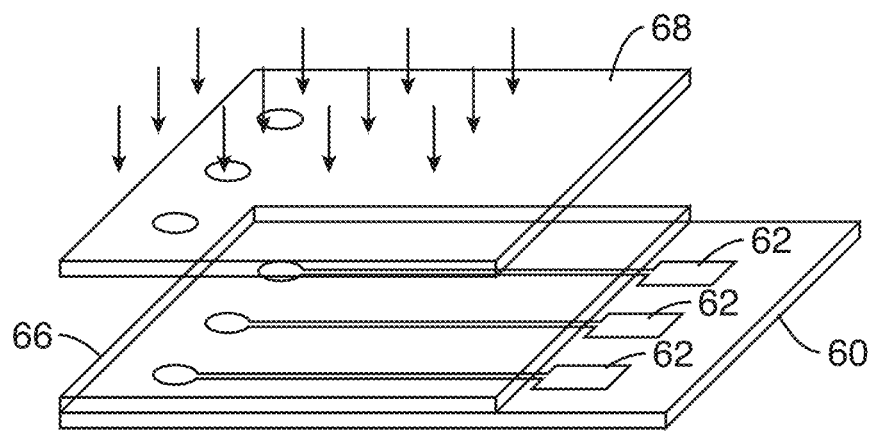

FIG. 5A through FIG. 5D illustrate a fabrication process for the printed flexible electrode array 12 of FIG. 1. As shown in FIG. 5A, all routing and sensors 62 are first printed via inkjet nozzle 64 on polyethylene napthalate (PEN) substrate 60. Sintering may be used to fuse together gold nanoparticles in the ink to create conductive lines 62. Next, the entire plastic, including conductive lines 62, were encapsulated by spin coating a thin (0.2 μm) dielectric layer 66 (e.g. an amorphous fluoropolymer such as parylene, Cytop, etc.) except for masked external contact pads (FIG. 5B). In the next step shown in FIG. 5C, the sensors are exposed by a delicate laser cutting process in which parylene is removed from the surface with no damage to the underlying Au. This may be achieved via oxygen plasma etching using a shadow mask 68 to selectively etch the dielectric layer. In a final step (FIG. 5E), extra Au was ink-jetted on top of the sensors 14 in order to make them protrude above the surface to allow for better contact with the wound.

Figure 5D:
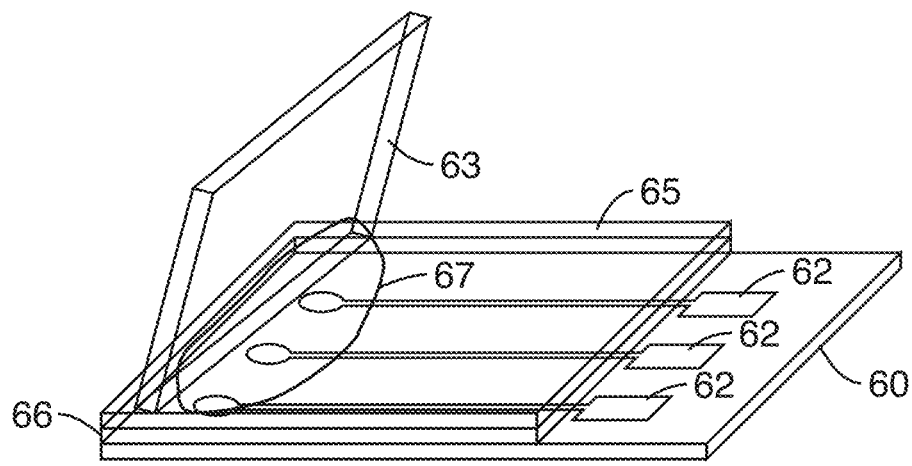
Figure 5E:
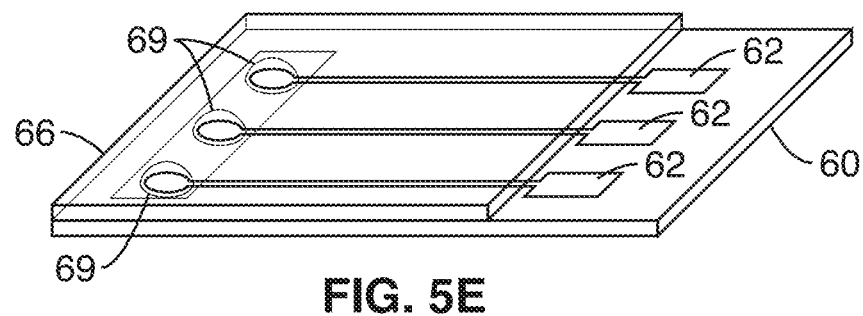

In an optional step shown in FIG. 5D, a thin layer 67 of highly conductive hydrogel was selectively printed onto the electrodes 14 using a silicone stencil 65, and wiped flush to stencil 65 with blade 63 to generate hydrogel bumps 69. The hydrogel may be used to reduce the contact impedance between the electrode and the tissue sample being measured, improving the reliability of the measurements.

Figure 6:
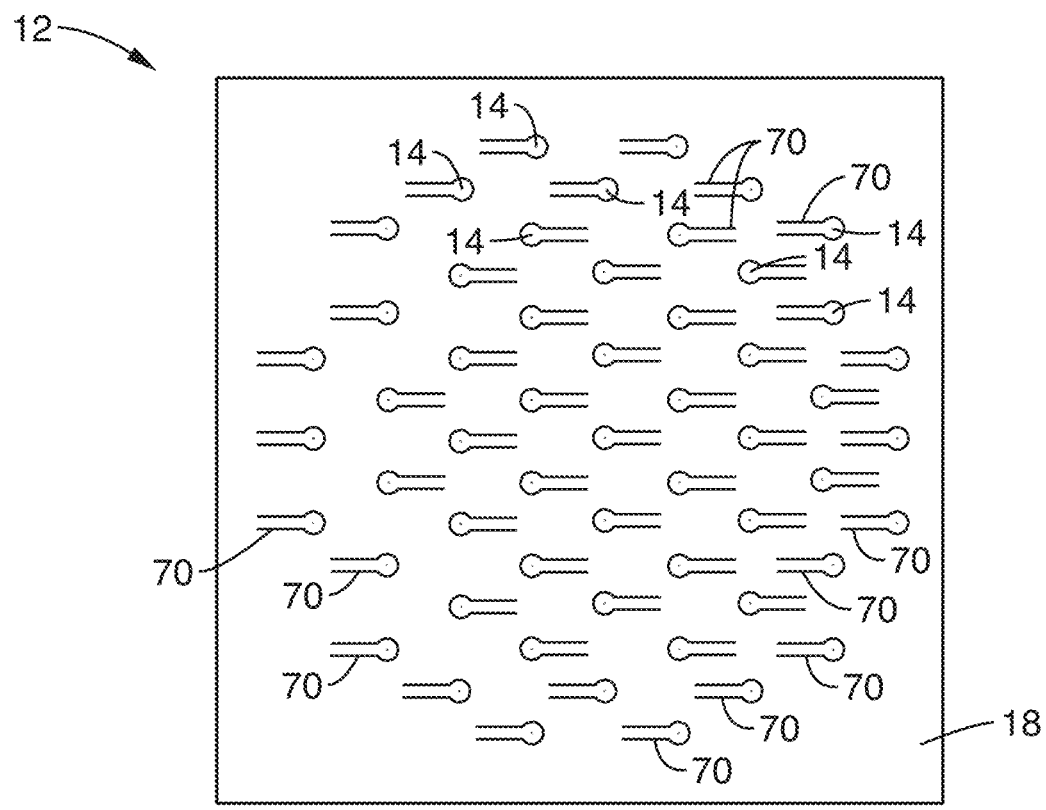
FIG. 6 illustrates a flexible electrode array comprising a plurality of "finger" flexures according to an embodiment of the technology disclosed herein.

FIG. 6 illustrates a flexible electrode array 12 comprising a plurality of "finger" flexures 70 according to an embodiment of the technology disclosed herein. To increase conformity to the applied anatomy, flexures 70 may be cut in the substrate 18. Several flexure patterns are contemplated. In the array 12 shown in FIG. 6, cuts 70 may be placed around each electrode 14 so each sits at the tip of a "finger" that can move in the z-direction towards the wound bed. In alternative embodiments (not shown), the substrate 18 can be removed at any space where there is no electrode or routing, or cut to resemble mesh and print electrodes, with routing to fit this pattern.

Figure 7:
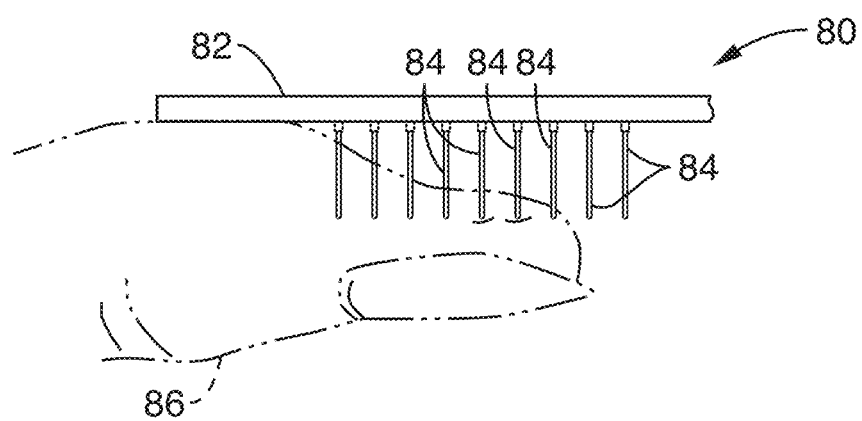
FIG. 7 shows an embodiment of a rigid electrode array board.

FIG. 7 shows an embodiment of a rigid electrode array board 80. The rigid array board 80 comprises a rigid substrate 82 and a plurality of spring probes 84 extending from the sense electrodes 14, essentially allowing the electrodes 14 to conform to the patient/wound topology 86.

Both the rigid and flexible versions of the electrode array boards are configured to make contact with the wound bed as well as healthy skin surrounding the wound. During operation, the array control hardware (control board 20) selects two electrodes 14 in the array 12 and performs an impedance measurement across these electrodes using the precision LCR/LCZ meter 40. By cycling through pairs, all of the nearest neighbors of the array can be sampled and a map of the impedance measurements can be constructed (FIG. 9).

Figure 8A:
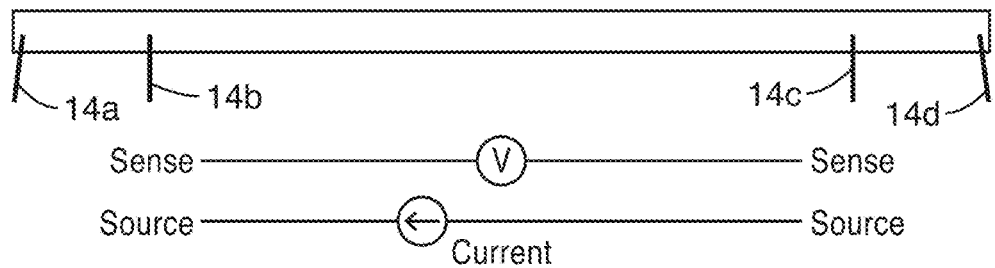
FIG. 8A shows a 2-point sensor configuration in which drive and sense signals are sent/received via two electrodes.
Figure 8B:
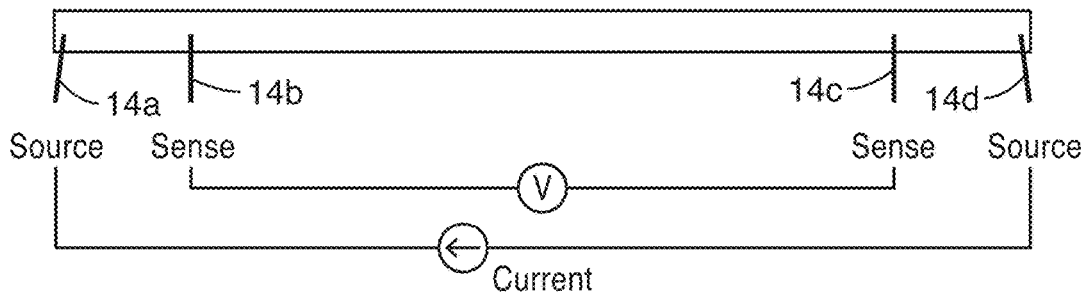
FIG. 8B shows a 4-point sensor configuration in which drive signals are sent via two electrodes and sense signals are sent via two other electrodes.

Referring now to the schematic diagram of FIG. 8A and FIG. 8B, nearest neighbor electrodes are chosen as the sense electrodes in a 2-point or 4-point measurement configuration. FIG. 8A shows a 2-point sensor configuration 12a, in which drive and sense signals are sent/received via two electrodes (14b and 14c). FIG. 8B shows a 4-point sensor configuration 12a, in which drive signals are sent via two electrodes (14a and 14d), and sense signals are sent via two other electrodes (14b and 14c).

Example 1

FIG. 9A through FIG. 18C illustrate a first experiment to verify the efficacy and function of the systems and methods detailed above.

Figure 9B:
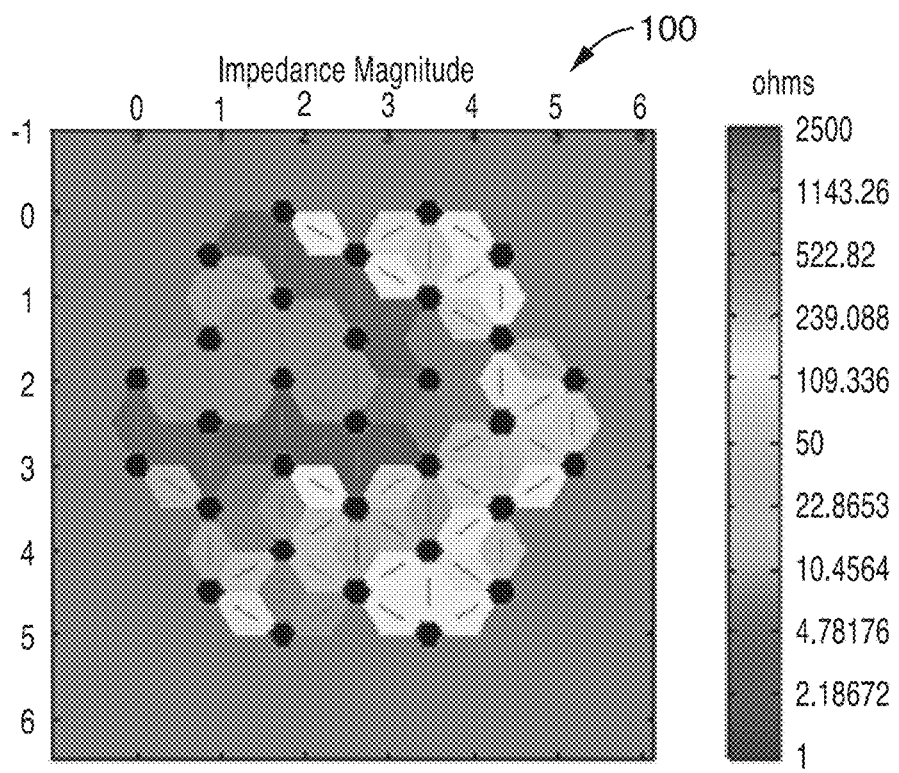

To visualize the impedance magnitude and phase data collected, a map 100 resembling the electrode array is created and shown in FIG. 9B. FIG. 9A illustrates an electrode array 12 according to an embodiment of the technology disclosed herein overlaid on a photo of the wound area 86 and example impedance map 100. In FIG. 9A, black dots mark the locations of all the sense electrodes 14 of array 12. Since measurements are taken between each pair of nearest neighboring electrodes 14, the space between each pair of electrodes can be filled in with a color that corresponds to the impedance magnitude or phase as determined by an intuitive color scale. Since the impedance over healthy skin is much higher than that of wounded skin, coloring the map 100 as shown in FIG. 9B according to impedance magnitude creates a visually intuitive look at the wound's appearance from an objective measurement.

To verify accuracy of the impedance measurements against visual analysis, registration marks corresponding to the border of the array 12 are marked/stained into the skin when applied to the wound area onto the skin to establish the position of the electrodes with respect to the pressure ulcer being measured. An image of the electrode array 12 is later superimposed onto a photo of the wound area. This makes clear which electrodes are in contact with healthy skin versus wounded tissue, and thus this can be compared with the map 100 generated by the impedance measurements from the device.

Referring to FIG. 10A through FIG. 10C, an open skin wound on a rat model is formed by surgically excising the tissue. The impedance of the wound and the surrounding tissue is determined by placing the electrode array 12 over the wound 86, wherein the black overlay in FIG. 10A illustrates the location of the electrodes 14. The magnitude (|Z|) and the phase angle (θ) of the complex impedance was measured between each nearest-neighbor pair of electrodes (labeled A-EE), then plotted using a color gradient to create a "wound map" for magnitude 102 and phase 104. The impedance was collected at multiple frequencies, with the data shown in FIG. 10B measured at 15 kHz. FIG. 10C shows a reduction in the impedance magnitude in the excision wound compared to the surrounding skin.

Referring now to FIG. 11A through FIG. 11C, a pressure ulcer on a rat model was formed by gently tenting the skin and placing it between two magnets for a specified period of time to develop a pressure sore over the following 3 days. The complex impedance was measured as described above. The data was collected at 100 kHz, and wound maps for magnitude 106 and 108 show changes in the impedance magnitude and phase on the pressure ulcer compared to the surrounding skin.

Referring now to FIG. 12A through FIG. 12E, the same wound of tissue 86 is shown as was provided in FIG. 10A through FIG. 10C. Impedance was measured for each electrode pair at several different frequencies, as described above. Here, two electrode pairs were selected: one pair 112 was located over the wound bed, and the second pair 110 was located over healthy skin. The magnitude (|Z|) (plots 120 and 124) and the phase angle (θ) (plots 122 and 126) were plotted against the measurement frequency. As shown in FIG. 12A through FIG. 12E, the frequency response of the wound area differs from the frequency response of the healthy tissue, as the pole occurs at a lower frequency in the wound than in the healthy tissue.

Referring now to FIG. 13A through FIG. 13E, the same pressure ulcer is shown as was provided in FIG. 11. As with FIG. 12A through FIG. 12E, one electrode pair 112 was selected to measure the pressure ulcer, and one pair 110 was selected to measure the healthy tissue. The impedance magnitude (|Z|) (plots 130 and 134) and the phase angle (θ) (plots 132 and 136) were plotted, illustrating the change in the spectra corresponding to tissue damage.

Referring now to FIG. 14, the impedance vs frequency spectra (as shown in FIG. 13) were fit to a model transfer function in containing 2 poles (pole 1 shown in FIG. 15A and pole 2 shown in FIG. 15B) and 2 zeros (zero 1 shown in FIG. 15C and zero 2 shown in FIG. 15D). Using these fits, poles and zeros are estimated from the frequency spectra of impedance measurements from many electrode pairs. Each electrode pair is categorized based on its location as measuring healthy skin, measuring a pressure ulcer, or measuring the border of the pressure ulcer. The location of the poles and zeros can then be compared between groups. In this data, we see that the location of the poles is significantly different in healthy skin vs. a pressure ulcer.

Referring to the images of FIG. 16, magnets were used to create a pressure ulcer in a rat model (as described above) using a 3 hour ischemic cycle. Photographs (FIG. 16) and impedance measurements (FIG. 17A through FIG. 17B) were taken over a period of −1 hour after removing the magnets, during the time when the blood was flowing back into the tissue (reperfusion). Poles and zeros were estimated from the impedance spectra at each time point. The position of the low frequency pole (Pole 2) on healthy tissue was compared against pressure ulcer immediately after removing the magnets (FIG. 17A), after 5 minutes of reperfusion (FIG. 17B), and after 1 hour of reperfusion (FIG. 17C). The position of the pole in healthy tissue vs the tissue where pressure was applied is not significantly different until the 1 hour measurement. Because the change in the pole position does not occur until after reperfusion, the difference in the 'healthy' vs. 'wound' impedance spectra shown previously cannot be attributed to the change in blood volume. This supports the hypothesis that the change in the impedance is due to cellular damage.

Referring now to FIG. 18A through FIG. 18C, the severity of pressure ulcers on the rat model may be controlled by changing the length of time the pressure is applied. Here, pressure was applied only to the point of creating "reversible" pressure damage: a visible ulcer never formed in the region where pressure was applied in tissue 86 (indicated in the photo with marker dots M). However, impedance measurements shown in impedance magnitude map 140 and impedance phase map 142 can distinguish between the healthy skin and the "reversible" pressure damage, even when such damage is not visible. This illustrates the capability of impedance sensing to provide early detection of pressure ulcers. By identifying the early stages of tissue damage, clinicians could prevent the formation of severe ulcers by taking steps to relieve the pressure.

Example 2

FIG. 19 through FIG. 24B illustrate a second experiment to verify the efficacy and function of the systems and methods detailed above. Rats were sedated and the dorsal body hair was shaved and depilated with Nair to provide bare skin for impedance measurements. After the area was cleaned, the skin was gently tented up and placed between two disc-shaped magnets to create pressure ulcers. The animals returned to normal activity with the magnets in place for 1 hour or 3 hours, at which point they were sedated and the magnets were removed. Eleven of the 12 animals used in this study received the 1 hour treatment, and nine of the 12 animals received the 3 hour treatment.

Using fluorescence angiography to image real-time blood flow in the tissue, it was observed that relieving the pressure initially resulted in increased perfusion (reactive hyperaemia) as the blood returned to the affected tissue. When blood returns to the ischaemic tissue, it produces reactive oxygen species and free radicals that can accelerate cell death. In the tested model, 1 hour of pressure produced mild reversible tissue damage, and 3 h of pressure produced more severe irreversible damage. Following the ischaemic event, we tracked the wounds for at least 3 days using impedance spectroscopy. The system measured impedance using a 100-mVRMS constant voltage test signal at frequencies between $10^2$ and $10^6$ Hz across all nearest-neighbor electrode pairs on the array.

FIG. 19 illustrates the progression of a representative example of irreversible tissue damage created with a 3-hour ischemia cycle is shown on days 1-3. On day 1, a control measurement was taken before ulcer formation, t=0 h corresponds to measurements immediately following magnet removal, and t=3 h corresponds to measurements after 3 h of reperfusion.

The first row shows the transparent flexible electrode array in place over the wound, and the pressure area is indicated with a dashed circle. The outer ring of electrodes on the array was not used for the two-point impedance measurements shown here, and thus the hexagon overlaid on the image outlines the area corresponding to the impedance maps. Scale bar (1 cm) applies to all wound photos.

The second and third rows show maps of impedance magnitude and phase angle, respectively, measured across nearest-neighbor pairs with the flexible electrode array at a frequency of 15 kHz. The asymmetry in the surface map on day 3 is due to the rejection of one broken electrode.

The fourth row illustrates the damage threshold that is determined from the magnitude and phase data at each pair, and mapped across the array. The shaded region indicates tissue damage. On days 2 and 3, a region of tissue damage is detected that clearly correlates with the location of the developing pressure ulcer. FIG. 20A shows plots of impedance spectra for the wound shown in FIG. 19 of healthy skin before applying pressure, No damage' regions on days 1-3, and Damage' regions on days 2 and 3. A representative electrode pair was selected from each region. The markers indicate the measured data values, whereas the lines and the shaded regions indicate the estimated transfer function and the 95% fit confidence interval, respectively. As shown in the results of FIG. 20A and FIG. 20B, tissue appeared less capacitive and more conductive consistent with a loss of cell membrane integrity FIG. 20C and FIG. 20D show plots of impedance spectra for 'pressure' and 'no pressure' locations of reversible (1 h) and irreversible (3 h) pressure damage measured with the flexible array on day 2, averaged over all animals in the study. Markers indicate the average data values at each frequency, with error bars showing the s.e.m. $\eta_P$ electrode pairs went into the calculation of the average values, measured from wounds on $\eta_A$ animals. In FIG. 20C and FIG. 20D, it was observed that the dominant pole for the wounded tissue was at a lower frequency than for the healthy tissue.

Across all animals in the 3-h group (n=9), the impedance spectra for areas developing pressure ulcers were clearly distinguishable by day 3 (or earlier) from spectra for areas that were healthy. Qualitatively, wounded areas showed a decrease in impedance magnitude and phase angles closer to zero. To determine specific threshold values of impedance magnitude and phase that defined 'damaged tissue', we utilized impedance spectra collected with the flexible electrode array from 14 wounds on eight rats. We then used a contrast optimization process that identified 15 kHz as the frequency at which the maximum difference was observed in impedance between damaged and non-damaged tissue. We determined that a magnitude value of $|Z|=6$ k$\Omega$ and a phase window of $-30° \leq \varphi \leq -10°$ measured at 15 kHz was an effective threshold for identifying damaged tissue while avoiding false positive readings. The same threshold values were applied to all wounds, regardless of whether they belonged to the 1-h or 3-h treatment group. Any pair of electrodes whose magnitude was below the threshold and whose phase value fell within the specified window was labelled as 'damaged tissue'. In other words, the term 'damage' indicates regions where impedance data predicts tissue damage, whereas the term 'pressure' indicates data from any area of tissue subjected to magnet pressure. The phase requirement was included to make the damage parameter less susceptible to minor animal-to-animal skin variations than using magnitude alone (such as skin thickness, hydration status and so on), and thus improve the reliability of tissue classification. Spatial impedance data can thus be translated into a map of the tissue damage parameter that differentiates healthy tissue from a wound.

As shown in FIG. 19 and FIG. 20A through FIG. 20D, by day 2 (the day following the ischaemic event) the impedance sensor identified an area of tissue damage that correlates with the placement of the magnets. Not surprisingly, tissue damage within the pressure area is not uniform; an ulcer can be seen in the lower right region of the pressure area in the day 3 image in FIG. 19, and this region is also highlighted in the map of the damage threshold. The analysis shown in FIG. 19 and FIG. 20A through FIG. 20B was carried out for each wound on each animal in the study, and all animals in the 3-h treatment group produced similar results. The repeatability of the results across wounds on many animals is shown in FIG. 20C and FIG. 20D. Here the impedance spectra for reversible (1 h) and irreversible (3 h) pressure damage measured with the flexible array on day 2 were averaged over all animals in the study, excluding those killed before day 2. For each wound, each electrode pair was labeled either as 'pressure' or 'no pressure' depending on whether or not the electrodes measured tissue where pressure had been applied. (All pairs spanning the boundary of 'pressure/no pressure' were omitted.) The reduction in impedance magnitude and a phase angle closer to zero is clearly evident in this ensemble data for the 3-h pressure group.

The ability to detect and monitor a pressure ulcer that has already formed on a patient is valuable, but a key advantage of using impedance spectroscopy to detect pressure ulcers is early detection of tissue damage.

FIG. 21 and FIG. 22A and FIG. 22B illustrate how impedance maps may be used to identify mild, reversible pressure damage. FIG. 21 shows the progression of reversible pressure damage created with a 1-h ischemia cycle is shown on days 1-3. In the images of the first row, dashed circles indicate where the pressure was applied and dots represent the placement of the electrodes. Slight discoloration of the skin is observed immediately after removing the magnets, but no ulcer develops. Impedance magnitude and phase plots of the second and third rows were measured with the rigid printed circuit board array (e.g. sensor board 80 of FIG. 7 of the present description). As shown in the fourth row of FIG. 21, damage is detected electrically on day 2 even with no visible evidence of the pressure damage, demonstrating the early detection capability of the device. (The small abrasion to the right of the measured area was irritation from hair removal.) Only a small region of damage remains on day 3.

FIG. 22A and FIG. 22B show Bode diagrams illustrating the impedance magnitude and phase versus frequency of 'No damage' and Damage' regions on days 1-3. A representative electrode pair was selected from each region. The circle markers indicate the measured data values, whereas the lines and the shaded regions indicate the estimated transfer function and the 95% fit confidence interval, respectively.

Mild, reversible pressure damage was created using a 1-h ischemia cycle (as opposed to the 3-h ischemia cycle used above), then monitored with impedance measurements for 3 days. The skin appeared slightly white during reperfusion, but no visible ulcer developed in the following 9 days, indicating that any pressure-induced damage was truly reversible. The impedance measurements reveal a more nuanced story. Using the same impedance thresholds to detect damage that were used for irreversible damage, we found that the impedance sensor detected damaged tissue in the region of pressure application in just over half of the cases studied (6 out of 11 animals using the rigid array and 5 out of 7 animals using the flexible array), again with no false-positive results (FIG. 21). Owing to the expected animal-to-animal variation, it is hypothesized that the combination of pressure and duration used in the 1-h cases was sufficient to create tissue damage in some, but not all, animals. Histology of skin samples with 1 h of ischemia confirmed that the tissue was not damaged in all cases. Variation in damage severity was also observed in 3 h ischemia cases, with some ulcers reaching a stage II classification while others with the same treatment were only classified as a stage I ulcer3. This animal-to-animal variation observed for the 1-h pressure cases (as well as the non-uniform damage within the area of pressure application) explains why averaging the impedance of 'pressure' and 'no pressure' areas over many animals (FIG. 20B) obscures a meaningful result for the reversible damage case.

FIG. 23A through FIG. 23C illustrates early detection of pressure-induced tissue damage in a test where magnets were used to create a pressure ulcer model on rats in vivo. The following three outcomes in response to applied pressure: (1) severe, irreversible pressure damage is sustained creating a visible ulcer that is also detected with impedance spectroscopy (row a); (2) mild pressure damage is sustained that is not visible to the naked eye, but can be detected using impedance spectroscopy (row b); and (3) pressure is not sufficient to damage the tissue and, correspondingly, the impedance sensor does not indicate damage (row c).

FIG. 24A through FIG. 24B shows a series of images of histology of skin samples. Skin samples were collected for histology on days 1, 2, 3 and 9, and processed with haematoxylin and eosin staining. Samples a-d were taken from animals in the 1-h pressure treatment group, whereas samples e-h were taken from animals in the 3-h pressure treatment group. All images were taken with ×100 magnification. Image (a) showed normal-looking dermis and epidermis. Image (b) showed no signs of ulceration. Image c shows normal epidermis (1) with orthokeratosis (2). No signs of ulceration were found in images (c) and (d), both showing normal epidermis (1) with compact hyperkeratosis (3). Image (e) depicts early small ulceration (4). In images (f-h) loss of epidermis (5) and necroinflammatory debris (scab, 6) with inflammation (neutrophils and lymphocytes, 7) deeper in the dermis were present.

FIG. 23A through FIG. 23C also demonstrate that the rigid calibration and flexible printed sensor arrays produced similar results, but that the rigid arrays produced more complete damage maps because they were more robust during multiple measurement-disinfection cycles. The second observation—detecting changes in the tissue that cannot be seen by eye—demonstrates the sensitivity of impedance spectroscopy to physiological changes associated with ulcers and its applicability as an early detection method for pressure ulcers.

Histological cross-sections performed at various time points throughout the study (FIG. 23A through FIG. 23C and FIG. 24A through FIG. 24B) support the hypothesis that the alteration of cell membranes and tissue structure causes the observed impedance changes. Histological analysis was performed on tissue samples from reversible (1 h of ischemia) and irreversible (3 h of ischemia) pressure groups. Histopathological examination of the haematoxylin and eosin-stained sections showed focal compact hyperkeratosis and focal hypergranulosis in the area of magnet application in both 1 and 3 h groups. The skin samples from the 1-h application group showed no evidence of skin ulceration, while all samples taken after the 3-h magnet application period demonstrated ulceration. These lesions showed overlying necroinflammatory debris with serum crust, focal loss of epidermis, alteration of underlying collagen and had sparse to moderate amounts of mixed inflammatory infiltrate composed predominantly of lymphocytes and neutrophils. In some cases, the inflammatory infiltrate involved deeper dermis, skeletal muscle and fascia. These histological findings were consistent with the changes in tissue structure that are expected to cause changes in impedance.

The technology described herein can improve upon standard wound monitoring techniques in many ways. Current methods of wound monitoring include using a ruler, taking scaled photographs, and tracing the wound on a transparent sheet of plastic. These methods are very subjective and vary between clinicians. Even an individual doctor's experience can make a significant difference in his or her ability to discern certain features of a wound (edema, erythema, infection, condition of exudate, etc.). The technology of the present description represents an objective measurement tool. Further, it includes the ability to monitor wound progression remotely and identify visually undetectable features (i.e. granular tissue formation).

The above measurements confirm that it is possible to identify not only the size and shape of an excision by determining the border of the wound, but also differentiate between a moist wound (exposed wound bed, potentially pus and so on) and a healing, scab-covered wound. With a slight change in configuration, the system of the present disclosure can also be used to measure voltage at each electrode 14 with respect to a common reference, creating a map of the voltage and endogenous electric field across the wound.

Since cells can be directed to migrate with an applied electric field, it is possible that applying an electric field may assist in the healing process, e.g. as a therapy device. The device demonstrated here provides the capability to test the extension of these theories from cells to complex tissues in vivo. Thus, it could be adapted to sense the endogenous field, apply an external field and monitor the response of the tissue to the stimulus, providing much-needed evidence regarding the efficacy of electrical stimulation for healing chronic wounds.

Avoiding the formation of pressure ulcers currently relies on preventative monitoring of the patient's skin, often including only visual examination. The subjective nature of the examination and the lack of continuous monitoring can be overcome by the technology described herein. Other practices to prevent formation of ulcers involve specialized hospital beds and rigorous schedules to turn patients, which are costly, time-consuming, and labor-intensive. Impedance measurements at high-risk sites would allow for early detection of cell senescence or death, which are primary indicators of impending ulcer formation.

The technology of the present description is adaptable to a wide range of applications. Merely exploring monitoring of skin and associated injury, there are a number of ways that this technology can supplement and improve the current treatment paradigms. Beyond examining surface injuries, options for internal monitoring are countless.

Formation of pressure ulcers, particularly in hospital settings where patients are forced to lie down for extended periods of time, is a major healthcare cost that can be avoided. The technology described herein can be used to diagnose risk of pressure ulcer formation and detect formation before it occurs. Changes in skin impedance occur before irritation in the skin can be visually detected, thus this device can pick up those small changes before a damaging pressure ulcer forms. This device would be able to detect impending development of an ulcer at the skin using impedance measurements before it is necessarily visually discernible.

Adequate ways to objectively monitor cutaneous wound healing is also an unmet clinical need. The technology of the present description can be used to objectively identify clinically relevant parameters that indicate progression of wound healing (i.e. wound border/area). It also has the potential to provide information beyond what is currently possible, for example the formation of granulation tissue and other features on the cellular level. In this scenario, patients or their caretakers who are not clinically trained would also be able to participate in the monitoring of their wound. Since the circuit takes the measurements, patients or their caretakers would only need to be instructed on how to use the device once and from then on be able to take their own measurements and send them to their physician.

The technology of the present description can be used to monitor the progress of wound healing and inform clinical decisions regarding treatment of the wound. This technology could be used in a number of situations. For example, it could be used at the doctor's office to make the analysis of a wound (and its progression in the healing process) more objective. This device would also allow for non-clinically educated caretakers (i.e. family members) to analyze the wound without needing to set up a doctor's appointment. Furthermore, it could be used remotely to allow constant monitoring of a wound over time without needing to undress the wound.

The technology of the present description may also be incorporated into the current treatment paradigm (Wound VAC), which represents one of the standard-of-care options for wound treatment. This would allow for easy adoption of the product as it would simply add monitoring functionality to the current Wound VAC being used to treat patients all the time.

In this application, the flexible circuit can be placed beneath the sponge of the Wound VAC (or printed directly on the sponge) and pushed against the wound. The negative pressure applied from the bandage will provide excellent contact between the electrodes and the wound bed.

It is also appreciated that other sensing modalities (e.g. pH, oxygenation, etc.) may also be incorporated in the system of the present disclosure, either as a sole source of measurement, or in addition to the impedance spectroscopy methods detailed above.

In all of the above applications, integrating wireless capability into the system may also be implemented. For example, the array 22 may comprise a wireless transmission device for communication with the control board 20. Control board 20 may also be wirelessly coupled to either the impedance analyzer 40 or computer 50. This will allow for remote monitoring, one of the major advantages of our technology described herein. In this scenario, data can be collected on a more frequent basis than once a week and sent to a physician for analysis. With this feature, physicians can let a patient know when they must come into the doctor's office to redress a wound or treat an infection rather than having the patient come in consistently even when there is no issue.

Other external wound monitoring applications include burn wounds, diabetic foot ulcers, etc.

Beyond monitoring pressure ulcers and cutaneous wounds on the surface of the skin, this technology can also be applied to the monitoring of internal wounds (i.e. post-surgery or after bone break/fracture). As previously mentioned, flexible electrode array 12 may communicate wirelessly with the control board 20 (which may be placed outside the body). Treatment options may include, but are not limited to, internal would monitoring of ulcers, polyps, hernias, anastamosis, magnamosis, tumor border detection, etc. The electrodes placed inside the body are not only completely biocompatible, but they may be configured to readily dissolve in the body after the wound is healed, thus eliminating the need for a subsequent operation to remove the electronic monitoring device. This use would address a huge unmet clinical need, as there is no adequate non-invasive alternative to monitoring internal healing. For example, the flexible circuit could be integrated at the site of a healing bone break or recovering hernia operation.

Methods and apparatus have been described that utilize impedance spectroscopy to measure and characterize tissue health, thereby allowing physicians to identify high-risk areas of skin to prevent formation of pressure ulcers, or to objectively monitor progression of wound healing. Measurements can be taken across nearest neighbor electrodes in an array to create a visually intuitive map of electrical impedance, which has not yet been shown in any existing literature. Data visualization can be implemented by creating a map resembling the electrode array and filling in the spaces between every two electrodes with a color corresponding to the impedance magnitude or phase as determined by an intuitive color scale.

The technology of the present disclosure represents an objective measurement tool that includes the ability to monitor wound progression remotely and identify visually undetectable features.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for detecting changes in biological tissue structures, the apparatus comprising: (a) a substrate comprising an array of electrodes; (b) the substrate configured to be positioned across an area of biological tissue; (c) a controller coupled to the array of electrodes; and (d) a processor coupled to the controller; (e) a memory storing instructions executable by the processor; (f) the instructions, when executed by the processor, performing steps comprising: (i) acquiring electrical signals from the array of electrodes; (ii) processing the electrical signals to measure impedance across at least two electrodes in the array of electrodes; and (iii) creating a map of electrical impedance across at least a portion of the area of biological tissue.

2. The apparatus of any preceding embodiment, wherein creating a map of electrical impedance comprises mapping one or more of impedance magnitude and phase angle across the area of biological tissue.

3. The apparatus of any preceding embodiment, wherein the instructions, when executed by the processor, further perform steps comprising identifying a change in the spectra across the map, the change in spectra corresponding to tissue damage within the area of biological tissue.

4. The apparatus of any preceding embodiment, wherein the area of biological tissue comprises a wound surface.

5. The apparatus of any preceding embodiment, wherein the area of biological tissue comprises a pressure ulcer.

6. The apparatus of any preceding embodiment, wherein the impedance is measured across pairs of neighboring electrodes.

7. The apparatus of any preceding embodiment, wherein the controller includes at least one multiplexer configured to allow for specific selection of drive and sense electrodes in the array.

8. The apparatus of any preceding embodiment: wherein the controller is configured to connect the electrodes through the one or more multiplexers to an impedance measuring device; and wherein the impedance measuring device provides drive signals to the electrodes and calculates a complex impedance of the tissue.

9. The apparatus of any preceding embodiment, wherein the instructions, when executed by the processor, further performing steps comprising measuring impedance at various frequencies and analyzing any dispersion observed in the frequency response.

10. The apparatus of any preceding embodiment, wherein the instructions, when executed by the processor, further perform steps comprising providing electrical stimulation to specific sites on the area of biological tissue to promote tissue repair.

11. The apparatus of any preceding embodiment, wherein the instructions, when executed by the processor, further perform steps comprising establishing which electrodes are used as a sense pair (S+ and S−) and a corresponding drive pair (D+ and D−).

12. The apparatus of any preceding embodiment, wherein the instructions, when executed by the processor, further perform steps comprising cycling through all neighboring pairs in the array to generate the map of the measured impedance.

13. The apparatus of any preceding embodiment, wherein the array of electrodes comprises a flexible substrate.

14. The apparatus of any preceding embodiment: wherein flexures are cut in the substrate at locations corresponding to the array of electrodes; and wherein the flexures allow the electrodes to be displaced away from the substrate and toward the biological tissue.

15. The apparatus of any preceding embodiment, wherein the array of electrodes comprises a conductive hydrogel disposed over the electrodes to promote contact with the biological tissue.

16. A method for detecting changes in biological tissue structures, the method comprising: positioning a substrate across an area of biological tissue, the substrate comprising an array of electrodes; acquiring electrical signals from the array of electrodes; processing the electrical signals to measure impedance across at least two electrodes in the array of electrodes; and creating a map of electrical impedance across at least a portion of the area of biological tissue; wherein said method is performed by executing instructions, on at least one computer processor, said instructions residing in a non-transitory memory readable by the computer processor 17. The method of any preceding embodiment, the method further configured for: providing electrical stimulation to specific sites on the area of biological tissue to promote tissue repair.

18. The method of any preceding embodiment, wherein creating a map of electrical impedance comprises mapping one or more of impedance magnitude and phase angle across the area of biological tissue.

19. The method of any preceding embodiment, further comprising: identifying a change in the spectra across the map, the change in spectra corresponding to tissue damage within the area of biological tissue.

20. The method of any preceding embodiment, wherein the area of biological tissue comprises a wound surface.

21. The method of any preceding embodiment, wherein the area of biological tissue comprises a pressure ulcer.

22. The method of any preceding embodiment, wherein the impedance is measured across pairs of neighboring electrodes.

23. The method of any preceding embodiment, further comprising: multiplexing the electrical signals to allow for specific selection of drive and sense electrodes in the array.

24. The method of any preceding embodiment, further comprising: providing drive signals to the pair of electrodes and calculating a complex impedance of the tissue.

25. The method of any preceding embodiment, wherein processing the electrical signals comprises measuring impedance at various frequencies and analyzing any dispersion observed in a frequency response of the electrical signals.

26. The method of any preceding embodiment, wherein processing the electrical signals comprises cycling through all neighboring pairs in the array to generate the map of the measured impedance.

27. The method of any preceding embodiment: wherein the array of electrodes comprises a flexible substrate, and wherein positioning a substrate across an area of biological tissue comprises conforming the substrate to a surface of the biological tissue.

28. The method of any preceding embodiment, wherein the area of biological tissue is a wound surface.

29. A system for detecting changes in biological tissue structures, the apparatus comprising: (a) a substrate comprising an array of electrodes; (b) the substrate configured to be positioned across an area of biological tissue; (c) a controller coupled to the array of electrodes; (d) wherein the controller includes at least one multiplexer configured to allow for specific selection of drive and sense electrodes in the array; (e) an impedance measuring device coupled to the electrodes through the one or more multiplexers, wherein the impedance measuring device provides drive signals to the electrodes; (f) a processor coupled to the controller; (g) a memory storing instructions executable by the processor; (h) the instructions, when executed by the processor, performing steps comprising: (i) acquiring electrical signals from the array of electrodes; (ii) processing the electrical signals to measure impedance across at least two electrodes in the array of electrodes; (iii) calculating a complex impedance of the tissue; and (iv) creating a map of electrical impedance across at least a portion of the area of biological tissue.

30. The system of any preceding embodiment, wherein creating a map of electrical impedance comprises mapping one or more of impedance magnitude and phase angle across the area of biological tissue.

31. The system of any preceding embodiment, wherein the instructions, when executed by the processor, further perform steps comprising identifying a change in the spectra across the map, the change in spectra corresponding to tissue damage within the area of biological tissue.

32. The system of any preceding embodiment, wherein the area of biological tissue comprises a wound surface or pressure ulcer.

33. The system of any preceding embodiment, wherein the impedance is measured across pairs of neighboring electrodes.

34. The system of any preceding embodiment, wherein instructions, when executed by the processor, further perform steps comprising measuring impedance at various frequencies and analyzing any dispersion observed in a frequency response of the electrical signals.

35. The system of any preceding embodiment, wherein the instructions, when executed by the processor, further perform steps comprising cycling through all neighboring pairs in the array to generate the map of the measured impedance.

36. The system of any preceding embodiment, wherein the array of electrodes comprises a flexible substrate.

37. The system of any preceding embodiment: wherein flexures are cut in the substrate at locations corresponding to the array of electrodes; and wherein the flexures allow the electrodes to be displaced away from the substrate and toward the biological tissue.

38. The system of any preceding embodiment, wherein the array of electrodes comprises a conductive hydrogel disposed over the electrodes to promote contact with the biological tissue.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for early detection of pressure ulcers, the apparatus comprising:
   (a) a substrate comprising an array of electrodes;
   (b) the substrate configured to be positioned across an area of biological tissue;
   (c) a controller coupled to the array of electrodes; and
   (d) a processor coupled to the controller;
   (e) a memory storing instructions executable by the processor;
   (f) the instructions, when executed by the processor, performing steps comprising:
      (i) acquiring electrical signals from the array of electrodes;
      (ii) processing the electrical signals to measure impedance across at least two electrodes in the array of electrodes;
      (iii) creating a map of electrical impedance across at least a portion of the area of biological tissue, the map comprising an impedance magnitude map and impedance phase angle map;
      (iv) comparing the impedance magnitude map and impedance phase angle map against a damage threshold; and
      (v) identifying tissue within the area of biological tissue as one of:
   healthy tissue, mild reversible pressure damage, and irreversible pressure damage.

2. The apparatus of claim 1, wherein the instructions, when executed by the processor, further perform steps comprising identifying a change in impedance spectra across the map, the change in impedance spectra corresponding to tissue damage within the area of biological tissue.

3. The apparatus of claim 1, wherein impedance is measured across pairs of neighboring electrodes.

4. The apparatus of claim 1, wherein the controller includes at least one multiplexer configured to allow for specific selection of drive and sense electrodes in the array.

5. The apparatus of claim 4:
   wherein the controller is configured to connect the electrodes through the one or more multiplexers to an impedance measuring device; and
   wherein the impedance measuring device provides drive signals to the array of electrodes and calculates a complex impedance of the area of biological tissue.

6. The apparatus of claim 1, wherein the instructions, when executed by the processor, further performing steps comprising measuring impedance at various frequencies and analyzing any dispersion observed in a frequency response of the area of biological tissue.

7. The apparatus of claim 1, wherein the instructions, when executed by the processor, further perform steps comprising providing electrical stimulation to specific sites on the area of biological tissue to promote tissue repair.

8. The apparatus of claim 3, wherein the instructions, when executed by the processor, further perform steps comprising establishing which electrodes are used as a sense pair (S+ and S−) and a corresponding drive pair (D+ and D−).

9. The apparatus of claim 3, wherein the instructions, when executed by the processor, further perform steps comprising cycling through all neighboring pairs in the array of electrodes to generate the map of the measured impedance.

10. The apparatus of claim 1, wherein the array of electrodes comprises a flexible substrate.

11. The apparatus of claim 10:
    wherein flexures are cut in the substrate at locations corresponding to the array of electrodes; and
    wherein the flexures allow the array of electrodes to be displaced away from the substrate and toward the biological tissue.

12. The apparatus of claim 10, wherein the array of electrodes comprises a conductive hydrogel disposed over the array of electrodes to promote contact with the biological tissue.

13. The apparatus of claim 1, wherein the damage threshold comprises a specified magnitude value and phase window.

* * * * *